United States Patent
Lankhof et al.

(10) Patent No.: US 6,706,946 B1
(45) Date of Patent: Mar. 16, 2004

(54) DISPOSABLE ABSORBENT ARTICLE HAVING HYDROPHOBIC TOPSHEET AND IMPROVED LIQUID HANDLING PERFORMANCE

(75) Inventors: John Peter Lankhof, Kelkheim (DE); Mattias Schmidt, Idstein (DE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/979,419

(22) PCT Filed: May 9, 2000

(86) PCT No.: PCT/US00/12703

§ 371 (c)(1),
(2), (4) Date: Nov. 6, 2001

(87) PCT Pub. No.: WO00/69382

PCT Pub. Date: Nov. 23, 2000

(30) Foreign Application Priority Data

May 14, 1999 (EP) .............................................. 99108657

(51) Int. Cl.[7] .......................... A61F 13/15; A61F 13/20
(52) U.S. Cl. .................................. 604/375; 604/385.01
(58) Field of Search ................................ 604/378, 383, 604/385.01

(56) References Cited

U.S. PATENT DOCUMENTS

| | | | |
|---|---|---|---|
| 3,614,055 A | | 10/1971 | Douglas |
| 4,077,410 A | | 3/1978 | Butterworth et al. |
| 4,988,344 A | * | 1/1991 | Reising et al. |
| 5,558,655 A | * | 9/1996 | Jezzi et al. |
| 5,643,588 A | * | 7/1997 | Roe et al. |
| 5,807,371 A | * | 9/1998 | Toyoda et al. |
| 5,865,824 A | * | 2/1999 | Chen et al. |

FOREIGN PATENT DOCUMENTS

| | | |
|---|---|---|
| EP | 0 257 280 A1 | 3/1988 |
| EP | 0 312 118 B1 | 4/1989 |
| EP | 0 340 763 B1 | 11/1989 |
| EP | 0 359 501 B1 | 3/1990 |
| EP | 0 469 591 B1 | 2/1992 |
| EP | 0 598 204 B1 | 5/1994 |
| EP | 0 670 154 B1 | 9/1995 |
| WO | WO 91/14414 A1 | 10/1991 |
| WO | WO 95/05139 A1 | 2/1995 |
| WO | WO 95/10648 A1 | 4/1995 |
| WO | WO 96/16682 A1 | 6/1996 |
| WO | WO 96/28602 A1 | 9/1996 |
| WO | WO 99/25288 A1 | 5/1999 |

* cited by examiner

*Primary Examiner*—Weilun Lo
*Assistant Examiner*—Michele Kidwell
(74) *Attorney, Agent, or Firm*—Edward J. Milbrada; Eileen L. Hughett; Ken K. Patel

(57) ABSTRACT

The present invention provides an absorbent article which combines a hydrophobic topsheet with a good liquid acquisition performance. The absorbent article of the present invention comprises a topsheet, a backsheet, a liquid storage structure intermediate the topsheet and the backsheet, and a liquid handling structure intermediate the topsheet and the liquid storage structure. The topsheet of the present invention has a liquid retention of less than 150 mg for a test liquid having a surface tension of 33 mN/m. The liquid handling structure of the present invention has a basis weight to uncompressed caliper ratio of less than 100 grams per square meter per millimeter. The topsheet of the present invention may comprise a fiber coating such as fluoropolymers in order to lower the contact angle of the topsheet.

11 Claims, 7 Drawing Sheets

DISPOSABLE ABSORBENT ARTICLE HAVING HYDROPHOBIC TOPSHEET AND IMPROVED LIQUID HANDLING PERFORMANCE

1. FIELD OF THE INVENTION

The present invention relates to absorbent articles for retaining body fluids such as urine, menses, or faecal material, and in particular to their ability to acquire and retain aqueous based materials. The invention further relates to disposable absorbent articles such as baby diapers or training pants, adult incontinence products, and feminine hygiene products.

2. BACKGROUND

Disposable absorbent articles are well know from the art for receiving and retaining bodily discharges, such as urine, menstrual fluids, or faecal materials. Thereby, two basic mechanisms are relied on. First, the containment of such discharges is generally achieved by a gasketing functionality, such as through impermeable materials or construction of sealings between the article and—in most cases—the skin of the wearer. The other key mechanism is to retain the discharges within the absorbent article, generally achieved by using an absorbent structure to pick up the discharges. In most cases, the absorption mechanism is directed towards handling of the aqueous components of the discharges.

One of the key performance criteria against which a absorbent article has to deliver is the acquisition speed. Obviously, a fast liquid acquisition warrants a short time span between exudation and storage of the exudate. Another key performance criterion is the dryness of the user facing surface of the absorbent article. To match the wearing comfort of regular underwear, a dry touch of the user facing surface is desired.

Thereby, one of the key basis transport and storage phenomena is related to the capillary effects of the structures, whereby two properties of the materials used for constructing such structures are of critical importance. First, the porosity of the structure respectively of the materials comprised in that structure. A great number of prior art has been directed against optimising the porosity, or pore size, be this in fibrous structures, or foamed structures, or structures essentially made of particulate materials, or combinations thereof.

Second, the surface tension effects. Also here, a great number of prior art has been dealing with the surface energy of the materials used in such structures. Thereby it is generally accepted, that the "ultimate storage materials" have to be relatively hydrophilic, whereas the "initial acquisition" materials can be less hydrophilic to allow better rewetting properties. This, however, has to be balanced with pore size requirements to still allow rapid fluid pick up into the article. It has also been recognised in the prior art, that these properties have to be considered not only for the first wetting instance, but that also subsequent loadings have to be taken in consideration.

As a consequence, a number of prior art deals with creating "gradient structures" have been disclosed, whereby—in direction of the fluid flowing into the absorbent structure—the materials exhibit different degrees of hydrophilicity—optionally in combination with other parameter impacting on the capillary transport properties, such as porosity or pore size. This aims at allowing easy penetration of the fluid into the article whilst reducing the ability for rewetting.

The hydrophilicity requirement was readily fulfilled for natural fibre based structures, such as cellulose of fluff based structures. Also, "semi-synthetic" materials like viscose/rayon maintained a intrinsic hydrophilicity throughout the material making process until the use in such structures. Further, a certain family of synthetic materials exhibit a natural hydrophilicity like polyester-based materials or polyacrylate materials. However, a number of materials being otherwise suitable for applications in such structures were hydrophobic by nature, for example polyolefinic resins, such as polyethylene or polypropylene from which webs to be used as topsheet could be made.

Consequently, a significant effort was spent against rendering such materials sufficiently hydrophilic at least on their surface so as to allow good wettability. One approach is to apply surfactants to the surface only, and often these were readily removable from this surface. This was thought to be beneficial for rewetting properties, however, for subsequent loadings the surface was left hydrophobic, with the risk of poor performance such as leakage.

Such structures and materials are for example disclosed in EP-A-0.469.591 (Hamajima); EP-A-0.312.118 (Meyer); EP-A-0.670.154 (Everett); EP-A-0.257.280 (Luceri); EP-A-0.359.501 (Cadieux); WO 91/14414 (Newkirk); U.S. Pat. No. 3,614,055 (Mesek); U.S. Pat. No. 4,077,410 (Butterworth);

Attempts to bind specific surfactants more strongly to the surface are described in EP-A-0.598.204 (Garavaglia) or WO 95/10648 (Everhardt).

One further approach in the prior art attempting to address this issue was to incorporate surfactants into the resins of such polymers, and/or by "attaching" the surfactants more firmly to the surface to maintain the hydrophilicity over subsequent loadings, such as described in EP-0.340.763 (Hansen).

In WO 96/28602 (Quincy), wettable materials such as films or fibrous webs are described, with a hydrophobic surface having coating which includes a surface free energy modifier, such as a protein, and a surface-active agent, such as a polyethoxylated alkylphenol. Such materials aim at optimising the wettability and penetration of porous materials by fluids wetting such films or fibrous webs.

However, none of the aforementioned prior art documents provided an absorbent article that features a permanently hydrophobic topsheet and still exhibits fast liquid acquisition and a low rewet. In this context, it is to be noted that topsheets comprising a skin care composition have become very popular recently such as for example those taught in WO 96/16682 (Roe et al.). The user facing surface of these topsheets is—due to the hydrophobic nature of the skin care compositions—at least partially hydrophobic over the entire usage period.

To further improve the liquid handling properties of absorbent article comprising such hydrophobic topsheets, it has been taught in PCT/US97/20842 (Roe) to use an apertured carrier covered with skin care composition as the topsheet allowing to cover the entire area in between the apertures with a skin care composition.

Independent of the above liquid handling aspects, it has been another recent trend in the absorbent article field to provide absorbent articles with apertured topsheets over open structures in order to be able to acquire and store faecal materials such as for example those described in WO 95/05139 (Roe). Such open structures have large open pores to store faecal material. On the other hand, such large open pores limit the liquid handling capabilities of such open structures by reducing their capillary suction. More specifically, such open structures are less efficient in acquiring liquid from a overlying topsheet thereby drying out that topsheet.

It is an object of the present invention to provide an absorbent article which overcomes the problems posed by the prior art absorbent articles.

It is a further object of the present invention to provide an absorbent article with improved liquid handling performance having an fibrous, apertured topsheet.

It is a further object of the present invention to provide an absorbent article with improved liquid handling having a hydrophobic topsheet.

It is a further object of the present invention to provide an absorbent article with improved liquid handling having a low retention liquid in the topsheet.

It is a further object of the present invention to provide an absorbent article with improved liquid handling having a topsheet comprising a skin care composition.

It is a further object of the present invention to provide an absorbent article having a structure having large open pores under an apertured topsheet.

3. SUMMARY OF THE INVENTION

The present invention provides a disposable absorbent article having a transverse centerline, a first region, and a second region, said front region being positioned forward of said transverse centerline, said front region coming into contact with the front waist of the wearer during use, said back region being positioned backward of said transverse centerline, said back region coming into contact with the back waist of the wearer during use. Said disposable absorbent article comprises a liquid pervious, fibrous, structured carrier, a liquid impervious backsheet at least partially peripherally joined to said structured carrier, a liquid storage structure positioned intermediate said topsheet and said backsheet, and a liquid handling structure positioned intermediate said topsheet and said liquid storage structure. A portion of said liquid handling structure is positioned in said first region, a portion of said liquid handling structure is positioned in said second region. The disposable absorbent article of the present invention is characterised in that said structured carrier has a liquid retention of less than less than 150 mg for a test liquid having a surface tension of 33 mN/m, and said liquid handling structure has a basis weight to uncompressed calliper ratio of less than 100 grams per square meter per millimeter.

The present invention further provides a disposable absorbent article wherein said structured carrier is oleophobic has a liquid retention of less than less than 50 mg for a test liquid having a surface tension of 62 mN/m.

The present invention further provides a disposable absorbent article disposable absorbent article has a front region total product acquisition performance of more than 3.75 ml/s in the first gush and of more than 0.5 ml/s in the fourth gush.

The present invention further provides a disposable absorbent article wherein said disposable absorbent article has a front region Skin Hydration rewet value of less than 120 milligrams.

The present invention further provides a disposable absorbent article wherein said structured carrier has a contact angle with distilled water of more than 90°.

The present invention further provides a disposable absorbent article wherein said liquid handling structure has a compression resistance of at least 70% under an applied pressure of 1 Newton per square centimeter.

The present invention further provides a disposable absorbent article, wherein at least a part of that surface of said structured carrier which faces the wearer during use comprises a surface finish selected from the group of fluoropolymers, chlorofluoropolymers, silicone coating.

The present invention further provides a disposable absorbent article wherein said structured carrier comprises a plurality of apertures having a size of at least 0.2 mm$^2$.

The present invention further provides a disposable absorbent article wherein said structured carrier has a open area of more than 12%.

The present invention further provides a disposable absorbent article wherein said structured carrier comprises is a layer of nonwoven material.

The present invention further provides a disposable absorbent article wherein said structured carrier comprises a skin care composition which is at least partially transferable to the skin of the wearer during use.

4. BRIEF DESCRIPTION OF THE FIGURES

While the specification concludes with claims pointing out and distinctly claiming the present invention, it is believed the same will be better understood by the following drawings taken in conjunction with the accompanying specification wherein like components are given the same reference number and:

5. DETAILED DESCRIPTION OF THE INVENTION

The absorbent article of the present invention is described in the following by means of a variety of different embodiments and by means of a variety of different features. Further embodiments of the present invention may be obtained by combining features of one embodiment with features of another embodiment disclosed herein and/or with other features disclosed herein. These further embodiments are considered to be implicitly disclosed herein and hence form part of the present invention. It will be apparent to the skilled person that combinations of certain features may lead to non-functional articles not forming part of this present invention.

5.1 Absorbent Article

As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use and, preferably, to be recycled, composted or otherwise disposed of in an environmentally compatible manner). A "unitary" absorbent article refers to absorbent articles which are formed of separate parts united together to form a coordinated entity so that they do not require separate manipulative parts like a separate holder and liner. A preferred embodiment of an absorbent article of the present invention is the unitary disposable absorbent article, diaper 20, shown in FIG. 1. As used herein, the term "diaper" refers to an absorbent article generally worn by infants and adult incontinent persons and is worn about the lower torso of the wearer. The present invention is also applicable to other absorbent articles such as incontinence briefs, incontinence undergarments, absorbent inserts, diapers holders and liners, feminine hygiene garments, and the like.

5.2 Diaper

Figure 1:
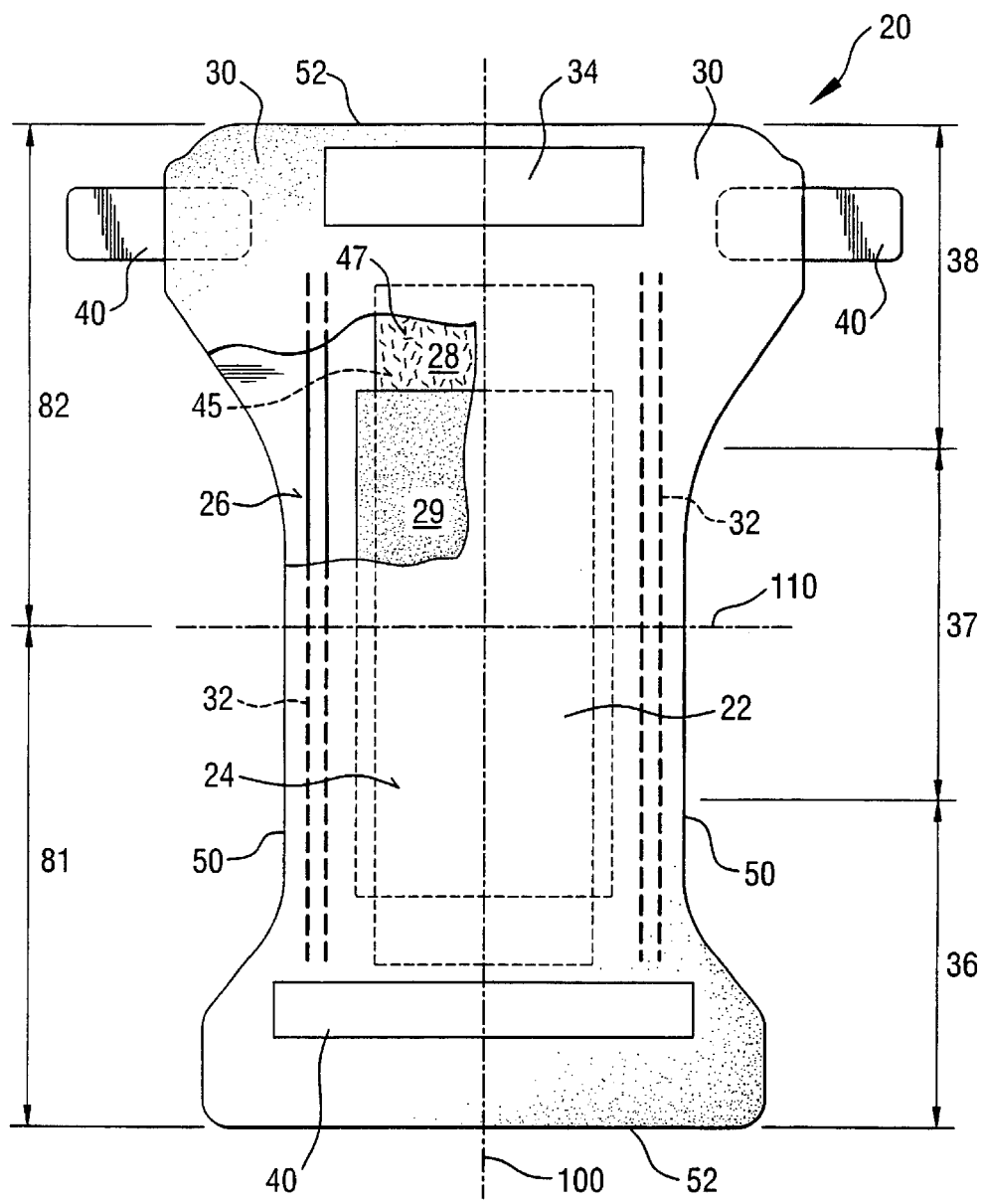
FIG. 1 is a plan view of an absorbent article embodiment of the present invention having portions cut away to reveal the underlying structure, the garment-facing surface of the diaper facing the viewer.

FIG. 1 is a plan view of the diaper 20 of the present invention in a flat-out, state with portions of the structure being cut-away to more clearly show the construction of the diaper 20. The portion of the diaper 20 which faces the wearer is oriented towards the viewer. As shown in FIG. 1, the diaper 20 preferably comprises a liquid pervious structured carrier 24; a liquid impervious backsheet 26; an liquid storage structure 28, which is preferably positioned between at least a portion of the structured carrier 24 and the backsheet 26; a liquid handling structure 29 positioned between the structured carrier 24 and the liquid storage structure 28; side panels 30; elasticised leg cuffs 32; an elastic waist feature 34; and a fastening system generally designated 40.

Diaper 20 is shown in FIG. 1 to have a front waist region 36, a rear waist region 38 opposed to the front waist region 36 and a crotch region 37 located between the front waist region and the rear waist region. The diaper 20 further has a first region 81 juxtaposed with the front of the wearer while the diaper 20 is being worn and a second region 82 opposed to the first region 81 and juxtaposed with the back of the wearer while the diaper 20 is being worn. The periphery of the diaper 20 is defined by the outer edges of the diaper 20 in which the longitudinal edges 50 run generally parallel to the longitudinal centerline 100 of the diaper 20 and the end edges 52 run between the longitudinal edges 50 generally parallel to the lateral centerline 110 of the diaper 20. In FIG. 1 the first region 81 is shown as extending from one end edge 52 to the lateral centerline 110 and the second region 82 is shown as extending from the opposing end edge 52 to the lateral centerline 110. For purposes of discussion, the lateral centerline 110 is shown as the boundary between the first region 81 and the second region 82 in FIG. 1. However, the boundary between the first region 81 and the second region 82 may be positioned at other locations, for example closer to one of the respective end edges 52. The first region 81 being juxtaposed with the front of the wearer should be superior in the handling of urine. The second region being juxtaposed with the back of the wearer should be superior in the handling of faecal material, in particular low-viscosity faecal material.

The chassis 22 of the diaper 20 comprises the main body of the diaper 20. The chassis 22 comprises at least a portion of the liquid storage structure 28 and preferably an outer covering layer including the structured carrier 24 and the backsheet 26. If the absorbent article comprises a separate holder and a liner, the chassis 22 generally comprises the holder and the liner. (For example, the holder may comprise one or more layers of material to form the outer cover of the article and the liner may comprise an absorbent assembly including a structured carrier, a backsheet, and an liquid storage structure. In such cases, the,holder and/or the liner may include a fastening element which is used to hold the liner in place throughout the time of use.) For unitary absorbent articles, the chassis 22 comprises the main structure of the diaper with other features added to form the composite diaper structure.

FIG. 1 shows an embodiment of the diaper 20 in which the structured carrier 24 and the backsheet 26 have length and width dimensions generally larger than those of the liquid storage structure 28 and the liquid handling structure 29. The structured carrier 24 and the backsheet 26 extend beyond the edges of the liquid storage structure 28 to thereby form the periphery of the diaper 20.

While the structured carrier 24, the backsheet 26, and the chassis 22 may be assembled in a variety of well known configurations, preferred diaper configurations are described generally in U.S Pat. No. 3,860,003 entitled "Contractible Side Portions for Disposable Diaper" which issued to Kenneth B. Buell on Jan. 14, 1975; and U.S. Pat. No. 5,151,092 issued to Buell on Sep. 9, 1992; and U.S. Pat. No. 5,221,274 issued to Buell on Jun. 22, 1993. Other suitable diaper chassis design are disclosed in U.S. Pat. No. 5,569,232 entitled "Absorbent Article With Multiple Zone Structural Elastic-Like Film Web Extensible Waist Feature" which issued to Roe et al. on Oct. 29, 1996; U.S. Pat. No. 5,554,144 entitled "Absorbent Article With Multiple Zone Structural Elastic-Like Film Web Extensible Waist Feature" which issued to Roe et al. on Sep. 10, 1996; U.S. Pat. No. 5,554,143 entitled "Absorbent Article With Multiple Zone Structural Elastic-Like Film Web Extensible Waist Feature" which issued to Roe et al. on Sep. 10, 1996; U.S. Pat. No. 5,554,145 entitled "Absorbent Article With Multiple Zone Structural Elastic-Like Film Web Extensible Waist Feature" which issued to Roe et al. on Sep. 10, 1996; U.S. No. Pat. No. 5,556,394 entitled "Absorbent Article With Multiple Zone Structural Elastic-Like Film Web Extensible Waist Feature" which issued to Roe et al. on Sep. 17, 1996. Each of these references is hereby incorporated by reference herein.

The inner surface of the diaper 20 comprises that portion of the diaper 20 which is adjacent to the wearer's body during use (i.e., the inner surface generally is formed by at least a portion of the structured carrier 24 and other components joined to the structured carrier 24). The outer surface comprises that portion of the diaper 20 which is positioned away from the wearer's body (i.e., the outer surface generally is formed by at least a portion of the backsheet 26 and other components joined to the backsheet 26) during use.

5.3 Aqueous Liquid Handling Performance

The liquid handling performance for aqueous liquids is a key feature of the present invention. The term "aqueous liquids" as used herein includes but is not limited to body exudates such as urine , faecal material, menses, blood, sweat.

5.3.1 Liquid Flow Path

To further explain the present invention, the following describes the fluid flow path through the absorbent article, from the "loading point" where the fluid first hits the article to the "ultimate storage region", i.e. that region of the article where the fluid is intended to be stored with minimal impact on the wearer. Modern diaper designs often use so called superabsorbent materials, but other structures comprising fluid binding means are also covered by the scope of the present invention.

When the fluid is first contacting the article, the so-called "acquisition phase", it is desirable to have the fluid penetrating into the pores/openings of the article as quickly as possible. This is enhanced by larger openings, and/or a hydrophilic surface of the material.

The next phase of the fluid handling in absorbent structures, the so-called storage phase", relates to transporting fluid to more or less remote locations for ultimate storage.

5.3.2 Liquid Flow Mechanisms

Generally spoken, liquid transport can be achieved by two mechanisms:

(1)—"free flow" whereby gravity is the driving force. This type of flow is enhanced by large open pores, and low surface energies, i.e. hydrophilic surfaces. However, this flow is per definition only in the direction of the gravity -which sometimes might be useful, but more often it is a accommodating for example different use situations such as position of the wearer etc.

(2)—"capillary flow" whereby capillary forces dominate. This flow mechanism allows to overcome the gravity dominated flow. One of the equations used to describe the capillary flow is the Laplace equation $$P_c = \frac{2\gamma\cos\theta}{R}$$

where $P_c$ is the capillary pressure, $\gamma$ is the surface tension of the liquid, $\theta$ is the contact angle between the liquid and the surface of the capillary, and R is the radius of the capillary.

It can readily be seen from this equation, that in order to increase the capillary pressure which is the driving force behind capillary flow, one needs to lower the contact angle by maximising the difference between the surface energy of the capillary and the surface tension of the liquid provide small capillaries increase the surface tension of the liquid to be transported, or—in other words—eliminate instances where the surface tension of the liquid is reduced However, there also exist constraints when designing an absorbent article which will be explained in more detail in the respective context.

5.3.3 Hydrophilicity

The disposable absorbent article of the present invention comprises materials of different hydrophilicities in order to optimise the fluid handling of the article.

One way to express hydrophilicity is via the contact angle measurement, whereby the angle is meant which is formed when a drop of liquid in on the surface of a solid material in an gas (generally air) environment. The more hydrophobic a material is, the larger the contact angle will be and—in the extreme—the fluid will form an almost spherical drop sitting on the surface. The more hydrophilic a material is, the more the fluid will spread, and—in the extreme —almost cover the surface as a thin film.

Often, materials having a contact angle of less than are called hydrophilic, of more than hydrophobic. For the exact scope of the present invention, however, the exact determination of the contact angle is not essential, but rather whether a certain material is treated such that it is more hydrophilic than the untreated material, such that when the difference in a certain measurement technique is larger than the accuracy of this method.

There exist a number of suitable materials for making fluid handling elements, which readily satisfy this requirement of being wettable, or sufficiently hydrophilic. In particular, naturally occurring materials, such as cellulose based fibrous materials, or cellulosic sponges, have a natural hydrophilicity, i.e. they have, due to their chemical composition (OH)-groups or other active sites on the surface resulting in specific surface energies as to allow to be readily wetted by aqueous fluids.

There exists, however, another group of materials which are relatively hydrophobic in their nature, such as by having due to their chemical composition only very few (OH)-groups or other polar sites on their surface. The most well known exemplifying materials are made of olefin polymers, such as polyethylene or polypropylene, but many other, including also bi-component structures comprising such materials can be contemplated. Conventional glues—and especially of the "hot-melt type"—generally comprise a number of different components, such as structural polymers, tackifiers, resins etc., most of these also being hydrophobic in nature.

In spite of their hydrophobicity such materials can still be attractive for being used in disposable absorbent articles for other reasons such as their broad availability, easy processing, the good disposability after use.

Thus, it is common state of the art, to overcome the hydrophobicity by treating such man-made hydrophobic polymers with hydrophilizing agents, or "surfactants", or surface active agents. These agents can be applied to the surface of the fibres, or webs, or film materials. As, for example, described in EP-A-0.340.763 (Hansen), the surfactants also can be incorporated into the resin at relatively low percentages, such that the (essentially hydrophobic) base resin (e.g. polypropylene) comprises from about 0.5% to 3% (on total weight basis) hydrophilizing agent. These hydrophilizing agents can be homogeneously distributed throughout the resin, or they can be distributed such that they have a higher concentration towards the surface, and even might not be present in detectable amounts in a region more remote from the surface, e.g. in the core of a fibre. Effective for the wettability is only the portion of the hydrophilizing agent on the surface of the material.

The liquid handling of the absorbent article of the present invention may be supported by comprising materials which exhibit increasing hydrophilicity along the flow path. Such a hydrophilicity gradient promotes liquid transport from one material onto the next by increasing the capillary pressure via contact angle decrements.

The first material in the liquid flow path, i.e. the material which comprises the loading point, is the structured carrier 24 of the absorbent article. This material is also the material which comes into contact with the skin of the wearer during use of the article. Because of the latter, it is desirable that the structured carrier is as dry as possible during use. Dryness of the structured carrier is basically governed by two factors, the liquid retention within the structured carrier and liquid coming back along the liquid flow path in the reverse direction. Deployment of a hydrophobic structured carrier improves its dryness with regard to both of these factors. If the capillary suction of the structured carrier is reduced by being hydrophobic, less liquid can be retained ion the pores of the structured carrier and liquid rewet from the lower layers is suppressed.

From a liquid acquisition point of view the hydrophobicity of the structured carrier is obviously detrimental. However, it has been found that when the structured carrier of the present invention is provided with apertures, i.e. macroscopic pores, it is possible to combine the feature of surface hydrophobicity with the overall liquid acquisition requirements of absorbent articles.

The liquid handling structure of the present invention which is placed immediately beneath the structured carrier needs to be at least partially hydrophilic to assist liquid acquisition through the apertures of the structured carrier. To promote liquid acquisition also for subsequent gushes, it is desired that the liquid handling structure of the present invention does not become substantially more hydrophobic during use.

The liquid storage structure of the present invention also needs to be hydrophilic and preferably more hydrophilic than the liquid handling structure in order to transfer liquid from the liquid handling structure into the liquid storage structure and in order to retain liquid within the liquid storage structure.

5.3.4 Pore Sizes

In order to transport the liquid along the liquid flow path it is desirable to provide different material with decreasing pore sizes along the flow path. Materials with a smaller pore size exhibit a higher capillary pressure than a material with a larger pore size. Thus, materials with smaller pores are able to actively acquire liquids from material with larger pores, in other words they are able to dewater the other material.

Hence, the absorbent article of the present invention preferably comprises different materials along the liquid flow path which exhibit a decreasing pore size in order to promote liquid transport along the flow path.

As already mentioned, the structured carrier of the present invention is required to have apertures to allow liquid penetration despite the hydrophobicity of the structured carrier. The liquid handling structure of the present invention preferably has large pores in order to allow quick acquisition of body exudates including medium and high viscosity liquids such as menses and faecal material. The liquid storage structure preferably has small pores in order to provide capillary suction to transfer and to store at least the aqueous components of the body exudates in the liquid storage structure.

5.3.5 Surface Tension of the Liquid

The effects of surface tension and surface energies of fluids and wetted materials on fluid transport properties have been widely discussed, such as in Chatterjee "Absorbency" (Elsevier, Amsterdam, 1985).

However, inventors have realised, that it is not only important to look at the wetting of the materials by the fluids, including the aim of maintaining the properties over subsequent wetting cycles, but also to look at the change of the properties of the discharged fluid and to exploit this finding to optimise the choice of materials for and their improved arrangement in absorbent structures.

From the Laplace equation above, it can be seen that a reduction of the surface tension of the liquid to be acquired is detrimental to the capillary pressure and the liquid handling of the different materials.

Hence, it is an optional feature of the present invention that the absorbent article maintains a high surface tension of the liquids, as they pass through the various hydrophilised materials of the absorbent article. In other words, it is optional element of the present invention that those elements of the absorbent article which are treated with surfactants to become more hydrophilic, not or only to a small extent loose these surfactants to the fluid.

Conventional agents such as commonly used Nonylphenol ethoxylates (NPE) can be readily removed, whilst materials according to the teachings of the present invention essentially do not reduce the surface tension of liquids passing through. This applies to all functional elements along the liquid flow path, structured carrier, liquid handling structure, and liquid storage structure.

Within the scope of the conventional surfactant technology, significant effort has already been spent against maintaining the hydrophilicity of the surface even after being in contact with an aqueous fluids, which attempt to wash away the surfactants. This can be achieved by getting a stronger bond between the (hydrophobic) polymer and the surfactant (such as described for example in EP-A-0.598.204 (Garavaglia) or WO 95/10648 (Everhardt)), or by replacing the surfactant which is washed away from the surface by diffusing mechanisms from the core of the polymer.

Furthermore, it is an optional element of the present invention to add materials to the absorbent structure to increase the surface tension of the penetrating fluid, so-called "scavenging agents", such as to maximise the wicking capability afterwards. The technologies for increasing surface tensions of fluids are available in different technology fields such as in the detergent area and the like. Essentially, there are two paths to achieve this. The first is by adding electrolytes to the solution. When doing so in the context of the present invention, care needs to be taken to not add contaminants for further fluid handling steps. For example, it is well known, that in particular two valent metal ions such as $Ca^{++}$ can have a detrimental effect on certain absorbency properties of the superabsorber. The second path to increase surface tension is to add high surface area agents such as activated carbon, zeolithes, and the like to the absorbent article. Such agents adsorb the surfactant at their surface thereby restricting the mobility of the surfactant. Such immobilises surfactant may not any longer migrate to the surface of the liquid thereby reducing the surface tension of the liquid.

5.3.6 Liquid Acquisition

The term "liquid acquisition" as used herein refers to the rate at which liquid which is deposited on top of the structured carrier of the present invention is absorbed from the surface of the structured carrier into the absorbent article.

The liquid acquisition performance of the absorbent article of the present invention is assessed via the Finished-Product-Acquisition Test as described hereinafter.

The absorbent article of the present invention has a liquid acquisition rate of at least 3.75 ml/s in the first gush, preferably of at least 4 ml/s in the first gush, more preferably at least 4.5 ml/s in the first gush, and most preferably at least 5 ml/s in the first gush. The absorbent article of the present invention further has a liquid acquisition rate of at least 0.5 ml/s in the fourth gush, preferably at least 0.6 ml/s in the fourth gush, more preferably at least 0.8 ml/s in the fourth gush, and most preferably at least 1.0 ml/s in the fourth gush.

5.3.7 Liquid Rewet

The term "liquid rewet" as used herein refers to already acquired liquid that is subsequently squeezed out through the structured carrier of a loaded absorbent article under pressure.

The liquid rewet performance of the absorbent article of the present invention is assessed via the Collagen Rewet Test as described hereinafter and is quantified by the Skin Hydration value.

The front region of the absorbent article of the present invention has a Skin Hydration value of less than 120 mg, preferably a Skin Hydration value of less than 90 mg, more preferably a Skin Hydration value of less than 70 mg, and most preferably a Skin Hydration value of less than 50 mg.

Optionally, the back region may have a Skin Hydration value of less than 120 mg, preferably a Skin Hydration value of less than 90 mg, more preferably a Skin Hydration value of less than 70 mg, and most preferably a Skin Hydration value of less than 50 mg.

5.3.8 Topsheet Wetness

In order to support the dry touch of the user facing surface of the absorbent article of the present invention, the absorbent article of the present invention preferably has a topsheet wetness of less than 300 mg, more preferably less than 200 mg, even more preferably less than 100 mg, even more preferably less than 80 mg, most preferably less than 50 mg according to the Topsheet-Finished-Product-Dryness disclosed hereinafter.

5.4 High Viscosity Liquid Handling

In addition, the absorbent article of the present invention preferably provides high viscosity liquid handling, and in particular liquid handling of viscous fluid body waste.

As used herein, the term "viscous fluid bodily waste" or "VFBW" generally refers to any waste discarded from the body which has a viscosity of greater than about 10 cP and less than about $2 \times 10^5$ cP at a shear rate of one 1/sec, (at about 25° C.), more particularly between about $10^3$ cP and $10^5$ cP at a one 1/sec shear rate, in a controlled stress rheometry test using parallel plates on a controlled stress rheometer. (For reference, water is at 1.0 cP at 20 degrees C. and Jif Creamy peanut butter (available from the Procter & Gamble Co., Cincinnati., Ohio) is approximately $4 \times 10^5$ cP at 25 degrees C. at this same shear rate). The method for determining viscosity, as used herein, is described in detail in the Test Method section below.

Once viscous fluid bodily waste has penetrated the liquid handling structure, it is desirable to store or hold the waste away from the wearer during the remainder of the wearing cycle and away from the caregiver during the changing process. As used herein, the term "store" refers to the physical separation of material deposited in a diaper from the body-facing surface of the article such that the material deposited in the diaper is not immediately in contact with or accessible to the wearer's skin. Storage Under Pressure, or "storage," is measured as the amount of material held in the structure on a unit area basis, as described in the Test Method Section below. If the Storage Under Pressure capacity is too low, the absolute quantity of viscous fluid bodily waste that can be stored away from skin access per unit area of the structure will be reduced. Adequate storage capacity is essential to reduce the probability of leakage and the area of skin contaminated by viscous fluid bodily waste because viscous fluid bodily waste that has been stored is less likely to be available to the body-facing surface of the structure for leakage and migration within the article.

In preferred embodiments of the present invention the absorbent article should include a liquid handling structure having a Storage Under Pressure value greater than about 800 grams per square meter ($g/m^2$) of the liquid handling structure of viscous fluid bodily waste. More preferably, the liquid handling structure should have a Storage Under Pressure value greater than about 900 $g/m^2$ of viscous fluid bodily waste. Even more preferably, the liquid handling structure should have a Storage Under Pressure value greater than about 1000 $g/m^2$ of viscous fluid bodily waste, and most preferably greater than about 1100 $g/m^2$ of viscous fluid bodily waste. Generally, Storage Under Pressure values between at least about 800 $g/m^2$ and about 10000 $g/m^2$, and between about 1000 $g/m^2$ and about 10000 $g/m^2$ have been found to be acceptable. (These preferred Storage Under Pressure parameters relate to integrated articles which are preferably evaluated as they are intended for use. Accordingly, all of the components or layers of the article should be configured as they would be during normal use when the measurement of their performance is made. A more detailed description of the method for determining Storage Under Pressure performance is included in the Test Methods section, below.)

Viscous fluid bodily waste that is accepted by, or penetrates, the absorbent article is preferably also retained in the diaper away from the wearer. One preferred way to retain bodily waste, especially viscous fluid bodily waste, is to immobilise the waste in a location away from the wearer. As used herein, the term "immobilise" refers to the ability of the material or structure to retain stored viscous fluid bodily waste under an applied pressure and/or the influence of gravitational forces. Immobilisation Under Compressed Inversion, or "immobilisation," may be accomplished by increasing the waste's viscosity (e.g., by dewatering), by mechanical entrapment (i.e., a surface energy phenomenon driven by increased surface area of contact of the viscous fluid bodily wastes with the internal regions of the material or structure) or by any other means known in the art. "Immobilisation Under Compressed Inversion," as described further in the Test Method Section below, is measured in terms of the percentage of the viscous fluid bodily waste or analogue that remains in the structure after the structure is subjected to an inverted pressure cycle, as described below. "Retention Under Compressed Inversion", or "retention," is an absolute measure of how much viscous fluid bodily waste remains "stored" under stressful usage conditions.

Preferably, the liquid handling structure should have a Retention Under Compressed Inversion value of greater than about 7.5 g of the viscous fluid bodily waste which penetrates the structure. More preferably, the liquid handling structure should have a Retention Under Compressed Inversion value of greater than about 8.0 g of viscous fluid bodily waste, and most preferably greater than about 8.5 g of viscous fluid bodily waste after being subjected to the Retention Under Compressed Inversion test, as described below. Generally, Retention Under Compressed Inversion values between at least about 7.5 g and about 100.0 g, and between about 8.0 g and about 100.0 g have been found to be acceptable. Under the same conditions, the liquid handling structure should have an Immobilisation Under Compressed Inversion value of at least 70% of the viscous fluid bodily waste accepted by the liquid handling structure. More preferably, the liquid handling structure should have an Immobilisation Under Compressed Inversion value of at least about 80% and most preferably at least about 85% of the viscous fluid bodily waste accepted by the element 120. Generally, Immobilisation Under Compressed Inversion values between at least about 70% and about 100%, and between about 80% and about 100% have been found to be acceptable. (These preferred Immobilisation and Retention Under Compressed Inversion parameters relate to integrated articles which are preferably evaluated as they are intended for use. Accordingly, all of the components or layers of the article should be configured as they would be during normal use when the measurement of their performance is made. A more detailed description of the method for determining Immobilisation and Retention Under Compressed Inversion performance is included in the Test Methods section, below.)

Without the appropriate immobilisation and retention performance, the effects of improved acceptance and storage performance may be diminished because the viscous fluid bodily waste may return to the body-facing surface of the structure, increasing the likelihood of leakage or contamination of the wearer's skin. Further, immobilisation is most effective if the structure first accepts the waste and then stores it. Viscous fluid bodily waste that is immobilised prior to being stored away from the wearer's skin may remain on the structured carrier in contact with the skin. Immobilising viscous fluid bodily waste which is in contact with the skin can increase the effort required by the caregiver during the changing/cleaning process and increases the likelihood of residual, micro-level contamination. "Micro-level contamination" refers to waste residue which remains on the skin, but is not easily visible to the human naked eye. Therefore, it may be helpful to consider at least three parameters (acceptance, storage, and immobilisation or acceptance, storage and retention) for a given structure when determining its utility for effectively managing viscous fluid bodily wastes.

In some embodiments, it may be desirable to provide the diaper 20 with different acceptance performance in different portions of the diaper. This may be accomplished by providing a single structured carrier which has been manufactured or treated to have regions of differing acceptance characteristics. Further, the structured carrier may be elevated above the plane of the body-facing surface of the article so as to be in better control of exuded viscous fluid bodily wastes. In some embodiments, it may even be desirable to have the structured carrier in contact with skin of wearer in proximity of the viscous fluid bodily waste source (e.g., the perianal region).

The trans-topsheet capacity as measured by the trans-topsheet capacity test as disclosed hereinafter reflects the diapers ability to handle low-viscosity faecal material. First region 81 and second region 82 of the diaper 20 should have a relatively high trans-topsheet capacity.

There is an inverse relationship between the minimum trans-topsheet capacity necessary to handle low-viscosity faecal material and the surface area of the diaper 20 having this minimum capacity. As a larger percentage of the diaper 20 surface area has a trans-topsheet capacity sufficient to handle low-viscosity faecal material, the necessary trans-topsheet capacity diminishes.

In any case, the first region 81 and the second region 82 of the diaper 20 preferably have a trans-topsheet capacity of at least about 300 grams per square inch provided that an surface area at least 0.02 square meter of the diaper 20 has such a trans-topsheet capacity and preferably at least 0.03 square meter of the diaper 20 has such a trans-topsheet capacity.

At least a portion of the first region 81 and at least a portion the second region 82 of diaper 20 according to the present invention preferably provides a trans-topsheet capacity of at least 300 grams per square meter, more preferably at least 400 grams per square meter, even more preferably at least 500 grams per square meter, still more preferably at least 600 grams per square meter, and most preferably at least 700 grams per square meter.

5.5 Liquid Storage Structure

5.5.1 Liquid Storage

The liquid storage structure 28 may be any absorbent means which is generally compressible, conformable, non-irritating to the wearer's skin, and capable of absorbing and retaining liquids such as urine and other certain body exudates. As shown in FIG. 1, the liquid storage structure 28 has a garment surface, a body surface, side edges, and waist edges. The liquid storage structure 28 may be manufactured in a wide variety of sizes and shapes (e.g., rectangular, hourglass, "T" -shaped, asymmetric, etc.) and from a wide variety of liquid-absorbent materials commonly used in disposable diapers and other absorbent articles such as comminuted wood pulp which is generally referred to as airfelt. Examples of other suitable absorbent materials include creped cellulose wadding; meltblown polymers including coform; chemically stiffened, modified or cross-linked cellulosic fibres; tissue including tissue wraps and tissue laminates; absorbent foams; absorbent sponges; superabsorbent polymers; absorbent gelling materials; or any equivalent material or combinations of materials.

The configuration and construction of the liquid storage structure 28 may also be varied (e.g., the liquid storage structure 28 may have varying calliper zones, a hydrophilicity gradient, a pore size gradient, a superabsorbent gradient, or lower average density and lower average basis weight acquisition zones; or may comprise one or more layers or structures). The total absorbent capacity of the liquid storage structure 28 should, however, be compatible with the design loading and the intended use of the diaper 20. Further, the size and absorbent capacity of the liquid storage structure 28 may be varied to accommodate wearers ranging from infants through adults.

Exemplary absorbent structures for use as the liquid storage structure 28 are described in U.S. Pat. No. 4,610,678 entitled "High-Density Absorbent Structures" issued to Weisman et al. on Sep. 9, 1986; U.S. Pat. No. 4,673,402 entitled "Absorbent Articles With Dual-Layered Cores" issued to Weisman et al. on Jun. 16, 1987; U.S. Pat. No. 4,888,231 entitled "Absorbent Core Having A Dusting Layer" issued to Angstadt on Dec. 19, 1989; and U.S. Pat. No. 4,834,735, entitled "High Density Absorbent Members Having Lower Density and Lower Basis Weight Acquisition Zones", issued to Alemany et al. on May 30, 1989.

5.5.2 Wrap Sheets

The liquid storage structure of the present invention may further comprise at least one wrap sheet. The wrap sheet covers the absorbent structure at least at a part of the surface of the absorbent structure, such that the fluid path from the liquid receiving area to the liquid storage structure will pass through the web. Thus the meaning of the term "wrapping" should not be read to mean complete wrapping or enveloping only. An example for such an embodiment can be a wrap-sheet covering the top surface of the liquid storage structure, and then being tacked down next to the core, such that the side surface can be but not necessarily have to be covered by the wrap sheet.

In a preferred embodiment, the wrap-sheet covers also other surfaces of the liquid storage structure, in one preferred embodiment, it covers all six surfaces, such that the liquid storage structure is completely enveloped. Another preferred and more easy to manufacture embodiment covers the top surface as well as two side surfaces by being folded around these to partly of fully cover the bottom surface.

The wrapping of the absorbent member can also be achieved by more than more than one wrap-sheet, or by one wrap sheet with different properties in different regions thereof. For example, the surface parts of the absorbent member which are not in the fluid flow path, can have no, or non-permanent fluid hydrophilicity. Or, a different wrap material can be used in such regions, or the absorbent member materials can there be contained by other elements, such as conventional tissue materials, but also impermeable sheets, which may at the same time has other functionality, such as a backsheet material.

Of course, it is an essential requirement, that the absorbent structure and the wrap sheet are in fluid communication with each other, such that the fluid flow path, and particularly the capillary transport gradient will not be interrupted. A preferred embodiment of this is a design, where the wrap sheet and the absorbent structure are in direct contact with each other—at least for the surfaces as described in the above.

It is generally known in the art, to manufacture suitable wrap sheets from tissue layers, nonwovens, and the like. Preferred nonwoven materials to be used for the wrap sheets of the present invention are disclosed for example in European patent application 98107288.7 (Fuchs). These hydrophilic materials exhibit a low surfactant release to the acquired liquid and hence do not negatively impact the liquid handling of the absorbent article of the present invention. In order to not negatively impact the liquid handling of the absorbent article of the present invention, a suitable wrap sheet has a surface tension reduction value of less than 15 mN/m, preferably less than 12 mN/m, more preferably less than 9 mN/, even more preferably less than 6 mN/m, and most preferably of less than 3 mN/m according to the surface tension reduction test defined hereinafter.

5.6 Backsheet

The backsheet 26 is positioned adjacent the garment surface of the liquid storage structure 28 and is preferably joined thereto by attachment means (not shown) such as those well known in the art. As used herein, the term "joined" encompasses configurations whereby an element is directly secured to the other element by affixing the element directly to the other element, and configurations whereby the element is indirectly secured to the other element by affixing the element to intermediate member(s) which in turn are affixed to the other element.

For example, the backsheet 26 may be secured to the liquid storage structure 28 by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. and marketed as HL-1258. The attachment means will preferably comprise an open pattern network of filaments of adhesive as is disclosed in U.S. Pat. No. 4,573,986 entitled "Disposable Waste-Containment Garment", which issued to Minetola et al. on Mar. 4, 1986, more preferably several lines of adhesive filaments swirled into a spiral pattern such as is illustrated by the apparatus and methods shown in U.S. Pat. No. 3,911,173 issued to Sprague, Jr. on Oct. 7, 1975; U.S. Pat. 4,785,996 issued to Ziecker, et al. on Nov. 22, 1978; and U.S. Pat. No. 4,842,666 issued to Werenicz on Jun. 27, 1989. Each of these patents is incorporated herein by reference. Alternatively, the attachment means may comprise heat bonds, pressure bonds, ultrasonic bonds, dynamic mechanical bonds, or any other suitable attachment means or combinations of these attachment means as are known in the art.

The backsheet 26 is impervious to liquids (e.g., urine) and is preferably manufactured from a thin plastic film, although other flexible liquid impervious materials may also be used. As used herein, the term "flexible" refers to materials which are compliant and will readily conform to the general shape and contours of the human body.

The backsheet 26 prevents the exudates absorbed and contained in the liquid storage structure 28 from wetting articles which contact the diaper 20 such as bedsheets and undergarments. The backsheet 26 may thus comprise a woven or nonwoven material, polymeric films such as thermoplastic films of polyethylene or polypropylene, or composite materials such as a film-coated nonwoven material. Preferably, the backsheet 26 is a thermoplastic film having a thickness of about 0.012 mm (0.5 mil) to about 0.051 mm (2.0 mils). Particularly preferred materials for the backsheet 26 include RR8220 blown films and RR5475 cast films as manufactured by Tredegar Industries, Inc. of Terre Haute, Ind. The backsheet 26 is preferably embossed and/or matte finished to provide a more cloth-like appearance. Further, the backsheet 26 may permit vapours to escape from the liquid storage structure 28 (i.e., be breathable) while still preventing exudates from passing through the backsheet 26.

5.7 Structured Carrier

The structured carrier 24 of the present invention has a first or inner surface oriented toward the interior of the disposable diaper, specifically oriented toward the liquid storage structure 28, and an opposed second or outer surface oriented toward the skin of the wearer when the diaper is worn.

The structured carrier 24 is juxtaposed with, but not necessarily adjacent the body surface of the liquid storage structure 28, and is preferably joined to the backsheet 26 or liquid storage structure 28 by means such as those well known in the art. In a preferred embodiment of the present invention, the structured carrier 24 and the backsheet 26 are joined directly to each other in the diaper periphery.

The structured carrier 24 is compliant, soft feeling, non-irritating to the wearer's skin, and has a fibrous structure. Further, the structured carrier 24 is liquid pervious, permitting liquids (e.g., urine) to readily penetrate through its thickness. A suitable structured carrier 24 may be manufactured from a wide range of materials, such as woven or nonwoven webs of natural fibres (e.g., wood or cotton fibres), synthetic fibres (e.g., polyester or polypropylene fibres), or a combination of natural and synthetic fibres. Preferably, the structured carrier 24 is made of a hydrophobic material to isolate the wearer's skin from liquids contained in the liquid storage structure 28.

5.7.1 General Properties 5.7.1.1 Functional Properties

The structured carrier of the present invention is hydrophobic and in order to minimise liquid retention in the structured carrier and to minimise liquid rewet from the liquid handling structure or the liquid storage structure back to the skin of the wearer.

Optionally, the structured carrier of the present invention may also be oleophobic in order to minimise liquid retention in the structured carrier and to minimise liquid rewet from the liquid handling structure or the liquid storage structure back to the skin of the wearer.

The structured carrier of the present invention has a liquid retention in the topsheet according to the Liquid-Retention Test defined hereinafter of less than 50 mg, preferably less than 40 mg, more preferably less than 30 mg, most preferably less than 20 mg for a test liquid having a surface tension of about 62 mN/m.

The structured carrier of the present invention has a liquid retention in the topsheet according to the Liquid-Retention Test defined hereinafter of less than 150 mg, preferably less than 120 mg, more preferably less than 90 mg, most preferably less than 70 mg for a test liquid having a surface tension of about 33 mN/m.

The contact angle of the user facing side of the structured carrier of the present invention with distilled water having a surface tension of at least 72 mN/m is at least 90°, preferably at least 100°, more preferably at least 110°, even more preferably at least 120°, most preferably more than 125°. High contact angles reduce the capillary suction of the pores of the structured carrier. Contact angles of more than 90° even result in a negative the capillary suction, hence rendering the respective pores water repellent.

5.7.1.2 Structural Properties

The structured carrier 24 preferably has a plurality of apertures with an effective aperture size of at least 0.2 square millimetres, more preferably, the plurality of apertures have an effective aperture size of at least 0.5 square millimetres, even more preferably, the plurality of apertures have an effective aperture size of at least 1.0 square millimetres, and most preferably, the plurality of apertures have an effective aperture size of at least 2.0 square millimetres. Effective apertures are those which have a grey level of 18 or less on a standard grey level scale of 0–255, under the image acquisition parameters described below.

The structured carrier 24 preferably has an effective open area of at least 12%, preferably of at least 15%, more preferably the structured carrier has an effective open area of at least 20%, even more preferably, the structured carrier has an effective open area of at least 25%, and most preferably the structured carrier has an effective open area of at least 30%.

A method to determine effective aperture size and open area is described in the method section.

5.7.2 Manufacturing Techniques

Suitable materials and structures for use as the structured carrier may include apertured fibrous webs such as nonwoven webs, woven webs, knitted webs, composites of the aforementioned materials, and the like. There are a number of manufacturing techniques which may be used to manufacture the structured carrier 24. For example, the structured carrier 24 may be a nonwoven web of fibres spunbonded, carded, wet-laid, meltblown, hydroentangled, combinations or composite laminates of the above, or the like. Preferred structured carriers 24 include a carded/carded composite, hydroentangled over a wire forming screen and thermally air-through bonded by means well known to those skilled in the nonwovens art and hydroentanglement of fibrous webs.

5.7.3 Surface Treatment

The structured carrier 24 of the present invention may comprise a surface finish reducing the surface free energy of at least a part of the surface of the structured carrier and hence rendering this part of the surface even more hydrophobic and eventually oleophobic.

The structured may comprise hydrophobicity gradients in a direction parallel to the major surfaces of the structured carrier to provide individual liquid handling properties in different regions of the structured carrier. The structured carrier may also comprise a hydrophobicity gradient in a direction perpendicular to the major surfaces of the structured carrier in order to enhance liquid transfer through the structured carrier.

At least a part of the surface, and in particular of the surface facing the wearer during use, of the structured carrier 24 of the present invention may comprise a surface coating such as a thin fluorocarbon polymer film. Suitable techniques to obtain such a surface coating are well known in the art and are described for example in European patent application No. 98116895.8, in WO 97/42356 (Gleason) and in WO96/00548 (Ouellette). Another suitable surface treatment is a silicone release coating from Dow Corning of Midland, Michigan available as Syl-Off 7677 to which a cross-linker available as Syl-Off 7048 is added in proportions by weight of 100 parts to 10 parts, respectively. Another suitable surface treatment is a coating of a UV curable silicone comprising a blend of two silicones commercially available from General Electric Company, Silicone Products Division, of Waterford, N.Y., under the designations UV 9300 and UV 9380C-D1, in proportions by weight of 100 parts to 2.5 parts, respectively. Another suitable treatments include fibre finishes available from Fibervisions of Varde, Denmark, under the designations T190 and T198, a fiber finish available from Schill and Seilacher of Böblingen, Germany, under the designation Silastol FC1760, a melt-in additive available from the Minnesota Mining And Manufacturing Company, of St. Paul, Minn., USA. Other suitable treatment materials include, but are not limited to, fluorinated materials such as fluoropolymers (e.g., polytetrafluoroethylene (PTFE), commercially available under the trade name TEFLON®) and chlorofluoropolymers. Other materials which may prove suitable for providing regions of reduced surface energy include Petrolatum, latexes, paraffins, and the like.

The structured carrier 24 of the present invention may comprises hydrophobic and oleophobic polymers. Processes to manufacture such polymers and articles therefrom is well known in the art and are described for example in U.S. Pat. No. 3,870,767 (Grimaud).

Optionally, the structured carrier of the present invention may be treated by modulated plasma glow discharge treatments as described in European patent application No. 98116895.8 (D'Agostino et al., P&G case CM1893FQ) and European patent application No. 98116894.1 (D'Agostino, P&G case CM1894FQ).

5.7.4 Skin Care Composition

The outer surface of the structured carrier may comprise an effective amount of a skin care composition which is semi-solid or solid at 20° C. and which is partially transferable to the wearer's skin. In preferred embodiment of the absorbent article of the present invention, the absorbent article additionally comprises an skin care composition which is at least partially transferable to the skin of the user during the intended use. Preferably, such an oil-containing composition is positioned on a user facing surface of the absorbent article. The oil-containing composition may also be deployed in such a way that it is only released at the time of intended use such as being microencapsulated.

Skin care compositions suitable for the absorbent article of the present invention are described for example in WO96/16682 (Roe et al.).

Preferably, the skin care compositions suitable for the absorbent article of the present invention have a melting profile such that they are relatively immobile and localised regarding their positioning within the absorbent article at room temperature, are transferable to the user at body temperature, and yet are not completely liquid under extreme storage conditions. Importantly, the skin care compositions of the present invention are easily transferable to the skin by way of normal contact, user motion, and/or body heat.

The skin care compositions suitable for the absorbent article of the present invention are solid, or more often semisolid, at 20° C., i.e. at ambient temperatures. By "semisolid" it is meant that the skin care composition has a rheology typical of pseudoplastic or plastic fluids. When no shear is applied, the skin care compositions can have the appearance of a semi-solid but can be made to flow as the shear rate is increased. This is due to the fact that, while the skin care composition contains primarily solid components, it also includes some minor liquid components.

The skin care compositions suitable for the absorbent article of the present invention are at least semi-solid at room temperature to minimise skin care composition migration. In addition, the skin care compositions preferably have a final melting point (100% liquid) above potential "stressful" storage conditions that can be greater than 45° C.

Specifically, the skin care compositions suitable for the absorbent article of the present invention should have the following melt profile:

| Characteristic | Preferred Range | Most Preferred |
|---|---|---|
| % liquid at room temp (20° C.) | 2–50 | 3–25 |
| % liquid at body temp. (37° C.) | 25–95 | 30–90 |
| final melting point (° C.) | >=38 | >=45 |

By being solid or semisolid at ambient temperatures, these skin care compositions do not have a tendency to flow and migrate into the interior of the absorbent article to which they are applied. This means less skin care composition is required for imparting desirable therapeutic or protective coating benefits.

When applied to the user facing surface of absorbent article of the present invention, the skin care compositions suitable for the absorbent article of the present invention are transferable to the user's skin by normal contact, user motion, and/or body heat.

A preferred embodiment of the absorbent article of the present invention contains an effective amount of an skin care composition. As used herein, the term "effective amount of an skin care composition coating" refers to an amount of a particular skin care composition which, when applied to a diaper structured carrier, will be effective in fulfilling their protective, therapeutic, or cosmetic intention. Of course, the effective amount of a skin care composition coating will depend, to a large extent, on the particular skin care composition used.

The skin care compositions suitable for the absorbent article of the present invention comprise: (1) an emollient(s); (2) an immobilising agent(s) for the emollient; (3) optionally a hydrophilic surfactant(s); and (4) other optional components.

The viscosity of the formulated skin care compositions, including emollient, immobilising agent, and optional components should be as high as possible to keep the skin care composition from flowing into the interior of the absorbent article. Unfortunately, high viscosities can also lead to skin care compositions that are difficult to apply without processing problems. Therefore, a balance must be achieved so the viscosities are high enough to keep the skin care compositions localised on the user facing surface of the absorbent article, but not so high as to cause processing problems. Suitable viscosities for the skin care compositions will typically range from about 5 to about 200 centipoises, preferably from about 15 to about 100 centipoises, measured at 60° C.

5.7.4.1 Emollient

The key-active ingredient in these skin care compositions is one or more emollients. As used herein, an emollient is a material that softens, soothes, supples, coats, lubricates, moisturises, or cleanses the skin. An emollient typically accomplishes several of these objectives such as soothing, moisturising, and lubricating the skin. For being suitable to be used in the absorbent article of the present invention, these emollients have either a plastic or fluid consistency at i.e., at ambient temperatures. This particular emollient consistency allows the skin care composition to impart a soft, lubricious, lotion-like feel.

Emollients useful in the absorbent article of the present invention can be petroleum-based, fatty acid ester type, alkyl ethoxylate type, fatty acid ester ethoxylates, fatty alcohol type, polysiloxane type, or mixtures of these emollients. Suitable petroleum-based emollients include those hydrocarbons, or mixtures of hydrocarbons, having chain lengths of from 16 to 32 carbon atoms. Petroleum based hydrocarbons having these chain lengths include mineral oil (also known as "liquid petrolatum") and petrolatum (also known as "mineral wax," "petroleum jelly" and "mineral jelly"). Mineral oil usually refers to less viscous mixtures of hydrocarbons having from 16 to 20 carbon atoms. Petrolatum usually refers to more viscous mixtures of hydrocarbons having from 16 to 32 carbon atoms. Petrolatum and mineral oil are particularly preferred emollients for skin care compositions of the present invention.

5.7.4.2 Immobilising Agent(s) for the Emollient

The immobilising agent counteracts the tendency of the emollient to migrate or flow into the absorbent article of the present invention by keeping the emollient primarily localised on the surface of the absorbent article to which the'skin care composition is applied.

Suitable immobilising agents for the use in the absorbent article of the present invention can comprise a member selected from the group consisting of $C_{14}$–$C_{22}$ fatty alcohols, $C_{12}$–$C_{22}$ fatty acids, and $C_{12}$–$C_{22}$ fatty alcohol ethoxylates having an average degree of ethoxylation ranging from 2 to about 30, and mixtures thereof. Preferred immobilising agents include $C_{16}$–$C_{18}$ fatty alcohols, most preferably selected from the group consisting of cetyl alcohol, stearyl alcohol, and mixtures thereof. Mixtures of cetyl alcohol and stearyl alcohol are particularly preferred. Other preferred immobilising agents include $C_{16}$–$C_{18}$ fatty acids, most preferably selected from the group consisting of palmitic acid, stearic acid, and mixtures thereof. Mixtures of palmitic acid and stearic acid are particularly preferred. Still other preferred immobilising agents include $C_{16}$–$C_{18}$ fatty alcohol ethoxylates having an average degree of ethoxylation ranging from about 5 to about 20. Preferably, the fatty alcohols, fatty acids and fatty alcohols are linear.

5.7.4.3 Optional Hydrophilic Surfactant(s)

It is important that the skin care composition also be sufficiently wettable to ensure that liquids can rapidly penetrate into at least the first component of the absorbent article. This diminishes the likelihood that body exudates will flow off the skin care composition coating rather than being drawn into at least the first component. Depending upon the particular immobilising agent used in the skin care composition of the present invention, an additional hydrophilic surfactant (or a mixture of hydrophilic surfactants) may, or may not, be required to improve wettability.

5.7.4.4 Other Optional Components

Oil-based compositions can comprise other optional components typically present in emollient, creams, and skin care compositions of this type. These optional components include water, viscosity modifiers, perfumes, disinfectant antibacterial actives, pharmaceutical actives, film formers, deodorants, opacifiers, astringents, solvents and the like. In addition, stabilisers can be added to enhance the shelf life of the skin care composition such as cellulose derivatives, proteins and lecithin. All of these materials are well known in the art as additives for such formulations and can be employed in appropriate amounts in the skin care compositions of the present invention.

5.8 Liquid Handling Structure

5.8.1 Properties

5.8.1.1 Positioning

The liquid handling structure is located between the structured carrier and the liquid storage structure. It is preferred that the liquid handling structure be operatively associated with the structured carrier such that fluid bodily waste acquired through the structured carrier may enter the liquid handling structure. In some alternate embodiments, the liquid handling structure may include a leg cuff, the waistband, a faecal waste containment pocket, or the like, or may be operatively associated with any such features.

A portion of the liquid handling structure is positioned in the first region of the absorbent article and a portion of the liquid handling structure is positioned in the second region of the absorbent article. In preferred embodiments, at least a part of the liquid handling structure is located in the region of the article that is near the wearer's urethra when worn. Further, at least a part of the liquid handling structure is preferably located in the region of the article that is near the wearer's anal region when worn. This helps ensure that any waste discharged is deposited on or near the liquid handling structure.

5.8.1.2 Functional Properties

The liquid handling structure of the present invention preferably is capable of accepting, storing, immobilising and retaining viscous fluid bodily waste that is accepted and stored by the absorbent article. These functions are described above in the context of the entire absorbent article of the present invention.

In addition, the liquid handling structure may transport viscous fluid bodily waste within the absorbent article 20 in directions generally parallel to the plane of the backsheet 26. The transport may be active, such that capillary or other forces result in the movement of the viscous fluid bodily waste or components thereof (e.g., free water). In other embodiments, the transport may be passive whereby viscous fluid bodily waste or components thereof move through the structure under the influence of externally applied forces, such as gravity, wearer pressure or wearer motion. In the case of passive transport, the liquid handling structure should have relatively large, interconnected channels, or the like, such that the viscous fluid bodily waste may readily move through the structure with minimum energy input.

The liquid handling structure of the present invention preferably does not reduce the surface tension of a liquid when the liquid handling structure is in contact with that liquid. Where needed, it is desirable to either use intrinsically hydrophilic materials such as cellulosic fibres, polyester fibres, or the like or to treat the hydrophobic materials with surfactants which are not easily released into the liquid.

5.8.1.3 Structural Properties

The liquid handling structure of the present invention has a ratio of basis weight to uncompressed calliper of less than 100 grams per square meter per millimetre, i.e. the liquid handling structure has an open structure in order to readily accept body exudates such as urine, menses, faeces, and the like. Preferably, the liquid handling structure of the present invention has a a ratio of basis weight to uncompressed calliper of less than 90 grams per square meter per millimetre. More preferably, the liquid handling structure of the present invention has a a ratio of basis weight to uncompressed calliper of less than 80 grams per square meter per millimetre. Most preferably, the liquid handling structure of the present invention has a a ratio of basis weight to uncompressed calliper of less than 70 grams per square meter per millimetre. Liquid handling structures having a ratio of more than 100 grams per square meter per millimeter may provide a sufficient openness to readily accept high viscosity liquids such as faeces and menses.

The liquid handling structure generally has a basis weight between 5 and 500 grams per square meter. Liquid handling structure having a basis weight of less than 5 $g/m^2$ will not be able to provide the desired resiliency and compression resistance. Liquid handling structure having a basis weight of more than 500 $g/m^2$ will add unwanted weight to the absorbent article which may cause discomfort by the wearer.

The liquid handling structure of the present invention generally has a calliper of at least 0.5 millimetres, preferably at least 1 millimetre. While even greater callipers would provide excellent handling of body exudates and in particular of low-viscosity faecal material, e.g. callipers of 5.0 centimetres, such callipers would create unwanted bulk in the diaper which may cause discomfort for the wearer.

Another key property is the resiliency of the liquid handling structure 29. In order to remain open, the liquid handling structure 29 must have a sufficient resiliency to withstand the forces of packaging and those applied by the wearer. Preferably, the liquid handling structure 29 has a resiliency of at least 50% after 30 seconds under an applied pressure of 1 $Newton/cm^2$, more preferably, the liquid handling structure 29 has a resiliency of at least 75% after 30 seconds under an applied pressure of 1 $Newton/cm^2$, most preferably, the liquid handling structure 29 has a resiliency of at least 85% after 30 seconds under an applied pressure of 1 $Newton/cm^2$.

Regardless of the makeup of the liquid handling structure, it should resist compression so as to maintain some significant level of capacity when a compressive force is applied to the liquid handling structure. Preferably, the liquid handling structure is able to maintain at least about 35% of its original thickness when a compressive pressure of 1 $Newton/cm^2$ is applied to the structure. More preferably, the liquid handling structure should be able to maintain at least about 50%, and most preferably at least about 70% of its original thickness when a compressive pressure of 1 $Newton/cm^2$ is applied. Generally, in preferred embodiments, the liquid handling structure is able to maintain between about 35% and 99% of its original thickness when a compressive pressure of 1 $Newton/cm^2$ is applied to the structure. More preferably, the liquid handling structure should be able to maintain between about 50% and 95% of its original thickness when a compressive pressure of 1 $Newton/cm^2$ is applied.

In order to not negatively impact the liquid handling of the absorbent article of the present invention, the liquid handling structure has a surface tension reduction value of less than 15 mN/m, preferably less than 12 mN/m, more preferably less than 9 mN/, even more preferably less than 6 mN/m, and most preferably of less than 3 mN/m according to the surface tension reduction test defined hereinafter.

5.8.2 Structure of the Liquid Handling Structure

The liquid handling structure may be any material or structure capable of accepting, storing, and immobilising bodily exudates, as described above. Thus, the liquid handling structure may include a single material or a number of materials operatively associated with each other. Further, the liquid handling structure may be integral with another element of the diaper 20 or may be one or more separate elements joined directly or indirectly with one or more elements of the diaper 20. Embodiments are contemplated wherein the liquid handling structure includes at least a portion of the core 28.

5.8.3 Suitable Materials

Suitable materials for use as the liquid handling structure may include large cell open foams, macro-porous compression resistant nonwoven highlofts, large size particulate forms of open and closed cell foams (macro and/or microporous), highloft nonwovens, polyolefin, polystyrene, polyurethane foams or particles, structures comprising a multiplicity of vertically oriented looped strands of fibres, liquid storage structure structures described above having punched holes or depressions, and the like. (As used herein, the term "microporou s" refers to materials which are capable of transporting fluids by capillary action. The term "macroporous" refers to materials having pores too large to effect capillary transport of fluid, generally having pores greater than about 0.5 mm in diameter and more specifically, having pores greater than about 1.0 mm in diameter.) One embodiment includes a mechanical fastening loop landing element, having an uncompressed thickness of about 1.5 millimetres available as XPL-7124 from the 3M Corporation of Minneapolis, Minnesota. Another embodiment includes a 6 denier, crimped and resin-bonded nonwoven highloft having a basis weight of 110 grams per square meter and an uncompressed thickness of 7.9 millimetres which is available from the Glit Company of Wrens, Ga. The liquid handling structure, or any portion thereof, may include or be coated with a lotion or other known substances to add, enhance or change the performance or other characteristics of the element.

5.8.3.1 Sheet Of Loop Material Having a Backing

Figure 2:
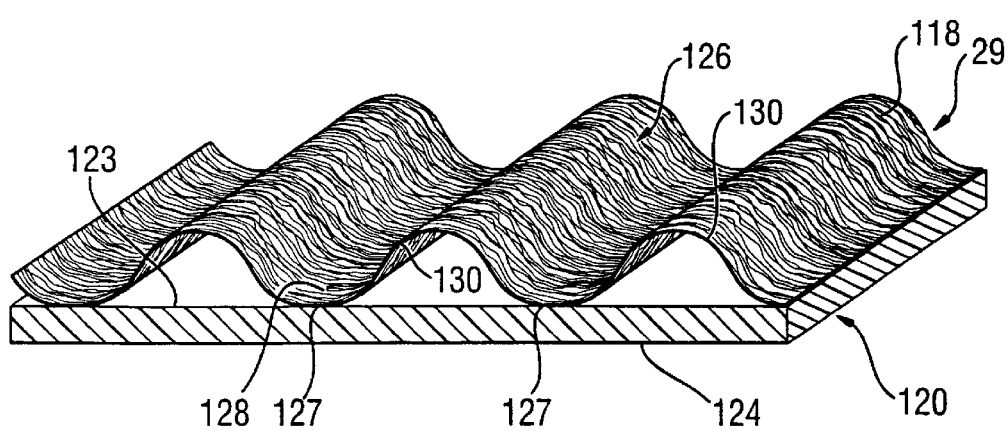
FIG. 2 is a perspective view of a liquid handling structure.

FIG. 2 shows one embodiment of a liquid handling structure 29. Generally the liquid handling structure 29 may be a sheet of loop material 118 having a backing 120 having front and rear major surfaces 123 and 124, and a multiplicity of longitudinally oriented fibres in a specially formed sheet of fibres 126 having generally non-deformed anchor portions 127 bonded by being embedded in the backing layer 120 at spaced elongate generally parallel bonding locations 128 that are continuous in one direction along the front surface 123 with arcuate portions 130 of the sheet of fibres 126 projecting from the front surface 123 of the backing layer 120 between the bonding locations 128 in continuous rows also extending transversely across the sheet of loop material 118. The arcuate portions 130 of the sheet of fibres 126 have a generally uniform height from the backing layer 20 of greater than about 0.5 millimetres and preferably greater than about 1.0 millimetres, the height of the formed sheet of fibres 126 is at least one third, and preferably one half to one and one half times the distance between the bonding locations 128, the individual fibres in the sheet of fibres 126 are less than 25 denier (preferably in the range of 1 to 10 denier) in size, and the sheet of fibres 126 without the backing 120 has a basis weight in the range of 5 to 300 grams per square meter (and preferably in the range of 15 to 100 grams per square meter) measured along the first surface 123 to provide sufficient open area between the fibres in the sheet of fibres 126 along the arcuate portions 130 (i.e., between about 10 and 90 percent open area) to afford ready penetration of faecal material into the individual fibres along the arcuate portions 130.

Suitable materials for use as the backing 120 include but are not limited to thermoplastic films, porous films, apertured films, apertured formed films, unapertured formed films, nonwoven webs, breathable materials, such as breathable films, including but not limited to microporous films, apertured nonwoven webs and the like. The backing 120 is preferably a relatively thin layer having a thickness in the range of about 0.00125 to 0.025 centimetres.

The fibres in the sheet of fibres 126 can be disposed in various directions with respect to the parallel bonding locations 128 and may or may not be bonded together at crossover points in the arcuate portions 130; can be disposed in various directions with respect to the parallel bonding locations 128 with the majority of the fibres in the sheet of fibres 126 (i.e., over 80 or 90 percent) extending in directions at about a right angle to the bonding locations 128; or all of the individual fibres in the sheet of fibres 126 can extend in directions generally at right angles to the spaced generally parallel bonding locations 128.

To be the most effective in the handling of body exudates and in particular low-viscosity faecal material the liquid handling structure must have a lofted open structure. One key component of this equation is the height of the arcuate portions 130 of the sheet of fibres 126 from the backing 120. As mentioned above the arcuate portions 130 of the sheet of fibres 126 have a generally uniform height from the backing 120 of greater than about 0.5 millimetres and preferably greater than about 1.0 millimetres.

5.8.3.2 Formed Film

Alternatively, a non-absorbent liquid handling structure 29 may be provided. If a non-absorbent liquid handling structure 29 is selected, it may be provided in the form of an apertured formed film meeting the calliper requirements described above. A suitable formed film is available from Tredegar Corporation of Terre Haute, Indiana under the designation X5790. Of course, if the liquid handling structure 29 is non-absorbent, it must be associated with a liquid storage structure 28 which has adequate capacity to absorb and retain the fluids deposited thereon.

5.9 Adhesives

It is generally known in the art, to attach at least a part of the surfaces of two mutually adjacent components of an absorbent article to each other by means of an adhesive.

In particular, where the interface between the two components is positioned somewhere along the liquid flow path, it is desirable to deploy a hydrophilic adhesive so as to not impede wettability of either one of the components. Preferably, a hydrophilic adhesive having a low surfactant release is used in order to not reduce the surface tension of the liquid during acquisition. Such an adhesive is described in a co-pending European patent application.

An adhesive suitable for the hygienic article of the present invention has a contact angle with Jayco synthetic urine of less than 70°, preferably less than 50°, more preferably less than 40°, most preferably less than 30°.

An adhesive suitable for the hygienic article of the present invention preferably reduces the surface tension of Jayco synthetic urine by less than 10 mN/m five hours after immersion into the synthetic urine, more preferably by less than 9 mN/m five hours after immersion, even more preferably by less than 8 mN/m five hours after immersion, even more preferably by less than 7 mN/m five hours after immersion, most preferably by less than 6 mN/m five hours after immersion.

An adhesive suitable for the hygienic article of the present invention may be obtained by blending a low level of a suitable surfactant into a suitable hydrophobic adhesive. Blending of the adhesive may be achieved by weighing the hydrophobic adhesive and the surfactant into a container, carefully heating the container to a temperature slightly above the melting point of the hydrophobic adhesive, stirring for approximately 10 minutes, and finally cooling down the mixture.

The specific concentration range of the surfactant depends on the specific adhesive and the specific surfactant use as is obvious to the skilled practitioner of the art. A too low surfactant concentration leads to a high contact angle of the adhesive with water, i.e. to a more hydrophilic adhesive. With a too high concentration of surfactant, the release of surfactant molecules into the liquid is increased. A surfactant concentration that has been found to be useful for the present invention is between 0.1% and 3% by weight, preferably between 0.2% and 2% by weight, more preferably between 0.25% and 1.5% by weight, most preferably between 0.5% and 1% by weight.

A hydrophobic adhesive that has been found suitable for the present invention is commercially available from H. B. Fuller Company of St. Paul, Minn., USA under the designation 1462. A surfactant that has been found suitable for the present invention is commercially available from Th. Goldschmidt AG of Essen, Germany, under the designation Tegotain D. The surfactant concentration that has been found useful for this specific combination of adhesive and surfactant is between 0.5% and 1% by weight.

It will, however, be apparent to the skilled practitioner of the art that many other combinations of adhesives and surfactants also satisfy the requirements of the present invention. This is particularly true for adhesive and surfactant belonging to the same chemical classes as the aforementioned examples. The present invention is intended to also cover these combinations.

5.10 Scavenger Agents

It is an optional feature of the absorbent article of the present invention to comprise a scavenging agent. The term "scavenging agent" refers to substances which are able to increase the surface tension of an aqueous solution of surfactants by suppressing the surface activeness of surfactants. Scavenging agents may function by restricting the mobility of the surfactants via, for example, adsorption.

Suitable surfactants include but are not limited to charcoal (preferably having a surface area of more than 900 $m^2/g$, commercially available from Carbo-Tech Aktivkohlen GmbH, Germany, under the designation PAK1000), zeolites (preferably having a surface area of at least 200 $m^2/g$, commercially available from Degussa AG, Germany, under the designation Aerosil 200), silica, and the like.

The scavengers may be placed at any suitable position along the liquid flow path and may be attached to the surface of any suitable component by any suitable means known in the art.

6. METHODS

Unless stated otherwise, all tests are carried out at about 22° C.+/−2° C. and at 35+/−15% relative humidity.

Unless stated otherwise, the synthetic urine used in the test methods is commonly known as Jayco SynUrine and is available from Jayco Pharmaceuticals Company of Camp Hill, Pennsylvania. The formula for the synthetic urine is: 2.0 g/: of KCl; 2.0 g/l of $Na_2SO_4$; 0.85 g/l of $(NH_4)H_2PO_4$; 0.15 g/l $(NH_4)H_2PO_4$; 0.19 g/l of $CaCl_2$; ad 0.23 g/l of $MgCl_2$. All of the chemicals are of reagent grade. The pH of the synthetic Urine is in the range of 6.0 to 6.4.

6.1 Finished-Product-Acquisition Test

Figure 3:
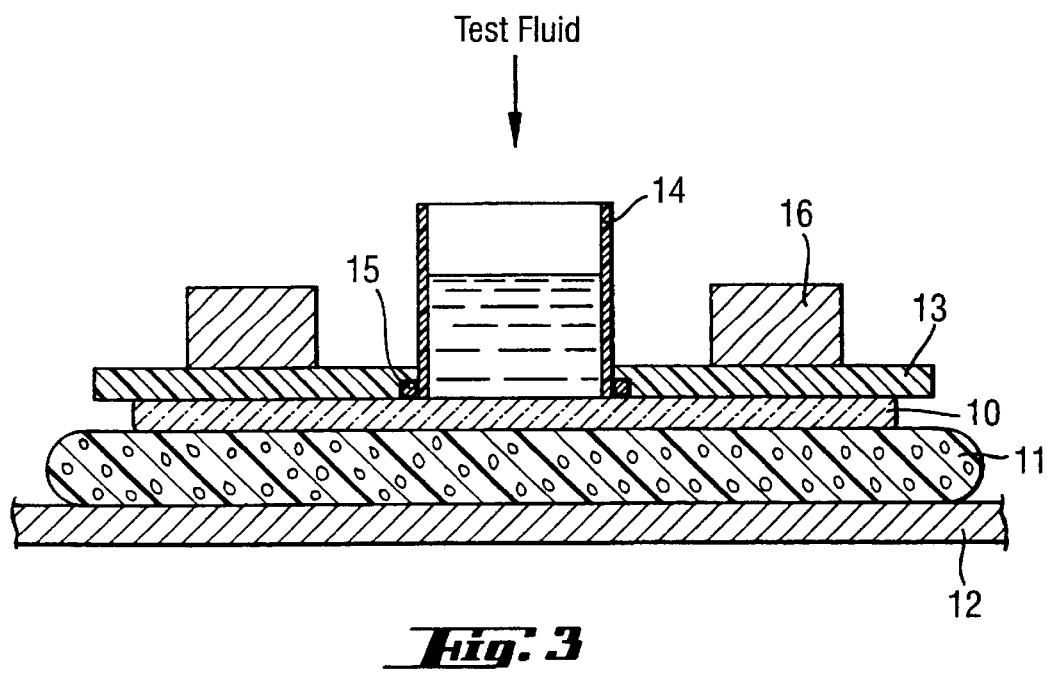
FIG. 3 is an illustration of the test set up for the Acquisition Test.

Referring to FIG. 3, an absorbent structure (10) is loaded with a 75 ml gush of synthetic urine at a rate of 15 ml/s using a pump (Model 7520-00, supplied by Cole Parmer Instruments., Chicago, USA), from a height of 5 cm above the sample surface. The time to absorb the urine is recorded by a timer. The gush is repeated every 5 minutes at precisely 5 minute gush intervals until the article is sufficiently loaded. Current test data are generated by loading four times.

The test sample, which comprises a core and includes a topsheet and a backsheet, is arranged to lie flat on a foam platform 11 within a perspex box (only base 12 of which is shown). A perspex plate 13 having a 5 cm diameter opening substantially in its middle is placed on top of the sample. Synthetic urine is introduced to the sample through a cylinder 14 fitted, and glued into the opening. Electrodes 15 are located on the lowest surface of the plate; in contact with the surface of the absorbent structure 10. The electrodes are connected to the timer. Loads 16 are placed on top of the plate to simulate, for example a baby's weight. A pressure of 50 g cm-2 (0.7 psi) is typically utilised in this test.

As test fluid is introduced into the cylinder it typically builds up on top of the absorbent structure thereby completing an electrical circuit between the electrodes. This starts the timer. The timer is stopped when the absorbent structure has absorbed the gush of urine, and the electrical contact between the electrodes is broken.

The acquisition rate is defined as the gush volume absorbed (ml) per unit time (s). The acquisition rate is calculated for each gush introduced into the sample. Of particular interest in view of the current invention are the first and the last of the four gushes.

This test is primarily designed to evaluate products having an absorbent capacity of about 300 ml to 400 ml. If products with significantly different capacities should be evaluated, the settings in particular of the fluid volume per gush should be adjusted appropriately to about 20% of the theoretical capacity, and the deviations should be recorded.

6.2 Topsheet-Finished-Product-Wetness Test

After executing the above described Finished-Product-Acquisition test with only two gushes and waiting for between 5 and 6 minutes, the topsheet is carefully removed (preferably as complete as possible) from the rest of the product and a piece of the topsheet is cut out with the acquisition point of the Finished Product Acquisition Test being substantially centered with respect to the cut-out piece. The topsheet piece should be 200 long and 120 mm wide. Then, the wet weight of the topsheet is measured. Finally, the topsheet is carefully dried (for example by heating in an oven at about 60° C.) and the dry weight of the topsheet is measured. The wetness of the topsheet is the difference between the wet weight and the dry weight of the topsheet.

6.3 Liquid Retention Test

The liquid retention test measures the liquid that is retained in a material sample that is temporarily immersed in a test liquid having defined surface tension. The test liquids are prepared by using distilled water and dissolving a suitable amount of suitable surfactant in the water.

A sample of the material having dimension of 50 mm length and 50 mm width is prepared and weighed. The sample is immersed in the test liquid for about 5 minutes. After taking the sample out of the test liquid, the sample is carefully shaken so that excess liquid can run off from the surface of the material sample.

The liquid retention of the material sample is obtained by measuring the wet weight and taking the difference between wet weight and dry weight.

6.4 Collagen Rewet Test Method

Before executing the test, the collagen film as purchased from NATURIN GmbH, Weinheim, Germany, is prepared by being cut into circular sheets of 90 mm diameter by using a sample cutter device and by equilibrating the film in the controlled environment of the test room (see above) for at least 12 hours (tweezers are to be used for all handling of the collagen film).

Figure 4:
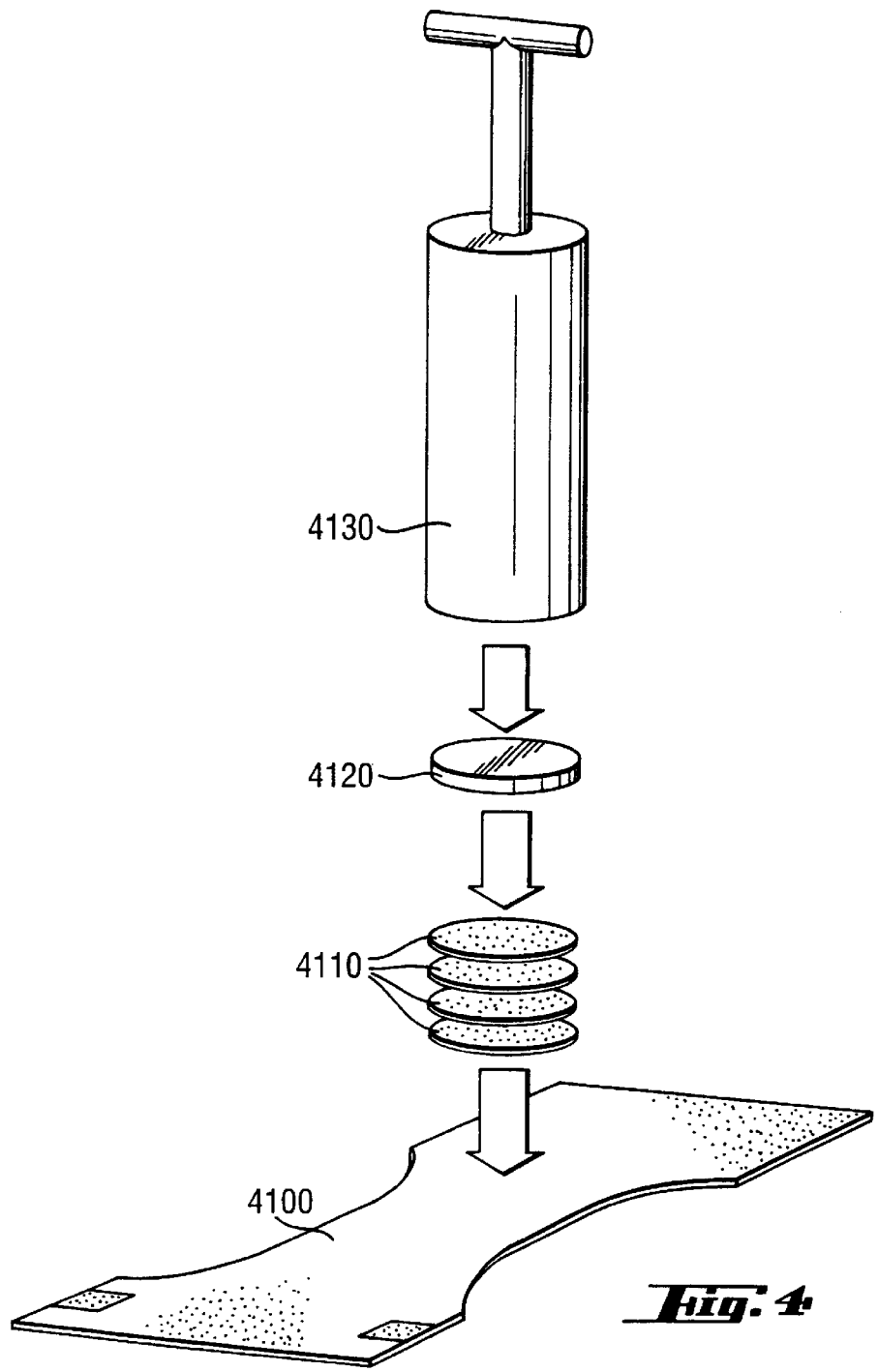
FIG. 4 is an illustration of the test set up for the Post Acquisition Collagen Rewet Method.

FIG. 4 shows the experimental center used for carrying out the collagen rewet test method.

At least 5 minutes, but not more than 6 minutes after the last gush of the above acquisition test is absorbed, the cover plate and weights are removed, and the test sample (4100) is carefully placed flat on a lab bench.

4 sheets of the pre-cut and equilibrated collagen material (4110) are weighed with at least one milligram accuracy, and then positioned centred onto the loading point of the article, and covered by perspex plate (4120) of 90 mm diameter, and about 20 mm thickness. A weight (4130) of 15 kg is carefully added (also centred). After 30+/−2 seconds the weight and perspex plate are carefully removed again, and the collagen films are reweighed.

The Skin Hydration Value is the moisture pick up of the collagen film, expressed in milligrams.

6.5 Preparation of Faecal Analogues 6.5.1 Faecal Analogue A

Analogue A is a faecal material analogue made by mixing 10 grams of Carbopol 941 available from the B. F. Goodrich Corporation of Brecksville, Ohio, or an equivalent acrylic polymer in 900 milliliters of distilled water. The Carpobol 941 and distilled water are weighed and measured separately. A 3-bladed marine-type propeller having a 2 inch diameter paddle, (available from VWR Scientific Products Corp. of Cincinnati, Ohio, Catalogue # BR4553-64, affixed to a ⅜" stirring shaft BR4553-52), is used to stir the distilled water. The propeller speed should be constant at 450 rpm during mixing. The mixer should form a vortex without splashing. The Carbopol is slowly sieved into the water so that it is drawn into the vortex and mixed without forming white clumps, or "fish eyes". The mixture is stirred until all of the Carbopol has been added, and then for a period of 2 minutes thereafter. The sides of the bowl containing the mixture should be scraped and the bowl should be rotated as needed to achieve a homogeneous mixture. (The mixture will likely be slightly cloudy with air bubbles). One hundred grams of a 1.0 N volumetric NaOH solution, available from J. T. Baker Co., Phillipsburg, N.J., is then slowly measured into the mixture and the mixture is stirred until homogeneous. The mixture should become thick and clear. The mixture should be stirred for 2 minutes after the addition of the alkali solution. The neutralised mixture should be allowed to equilibrate for at least 12 hours and should be used for the Trans Topsheet Capacity Test within 96 hours thereafter. Before the Carbopol mixture is used, it should be stirred in the container at low speed (about 50 rpm) for about 1 minute to ensure the mixture is homogeneous.

Analogue A should, if prepared correctly, have a shear viscosity of about 13000 Pascal seconds at a shear rate of 3,12 per second measured at a temperature of between 20 and 23° C.

6.5.2 Faecal Analogue B

The test analogue (Analogue B) used in this measurement is an aqueous polyacrylamide solution prepared as follows. Twenty-two and five-tenths (22.5 g) grams of polyacrylamide, available from Aldrich Chemical Company of Milwaukee, Wis. is mixed with a solution of 20 g of Dawn dishwashing solution, available from the Procter & Gamble Company of Cincinnati, Ohio, diluted with 1000 ml distilled water having a temperature of 90° C. Mixing is done using the same propeller used in mixing Analogue A, except that the propeller speed should be constant during mixing at about 650 rpm. Mixing is done for 30 minutes in a water bath at 80° C. The heated water bath is removed and the mixture is stirred for an additional 30 minutes. The mixture is allowed to equilibrate for at least 12 hours and used for the Immobilisation Under Compressed Inversion test within 96 hours. Analogue B should have a hardness value (measured as described below) of between about 7.5 and about 10.5 grams. Analogue B is designed to simulate the water suction power of actual runny faeces from breast-fed babies. Analogue B is generally easier to accept (i.e., more mobile) than Analogue A, which makes its retention more difficult.

6.5.3 Faecal Analogue C

The test analogue C used here is an aqueous polyacrylamide solution prepared as follows. 11.1 grams of polyacrylamide, available from Aldrich Chemical Company of Milwaukee, Wis. is mixed with a solution of 4.12 grams of FeClone #4, available from SilliClone Studios, USA, and 4.12 grams of FeClone #7, available from SilliClone Studios, USA, diluted with 906.5 ml distilled water. Mixing is done using the same propeller used in mixing Analogue A, except that the propeller speed should be constant during mixing at about 650 rpm. Mixing is done for 30 minutes in a water bath at 180F. The heated water bath is removed and the mixture is stirred for an additional 30 minutes. The mixture is allowed to equilibrate for at least 12 hours and used for the Fecal Acceptance Test within 96 hours. Analogue C should have a hardness value (measured as described below) of between about 3 and about 5 grams.

6.6 Hardness Method

Hardness is measured using a Stevens-Farnell QTS-25 Texture Analyser, model 7113-5 kg, and associated software on an Intel-based machine having a 486 processor or higher. A ½ inch stainless steel spherical probe and an analogue receptacle are provided. A suitable probe is the TA18 probe available from Leonard Farnell Co. of Hatfield, England. The analogue receptacle can be made by cutting a 7 milliliter linear low density polyethylene scintillation vial (having an inside diameter of 0.55 inches+/−0.005 inches) to about 16 millimetre length. Suitable vials are available from Kimble Glass Company of Vineland, N.J. as #58503-7 vials. The analogue receptacle is filled to the top edge (level) with the analogue (Analogue A or B, as described below) or faeces to be tested. If a modification agent is to be evaluated, the sample is prepared via the Sample Preparation Method described below. The vial is centred under the ½ inch spherical stainless steel probe. The probe is lowered such that it just contacts the surface of the analogue in the vial. The probe 5162 is moved downward 7 millimetres at about 100 millimetres per minute and then stopped. The Hardness is the maximum recorded resistive force encountered by the probe on its 7 millimetre stroke. (The temperature of the room and the analogue should be between about 65 to 75 degrees Fahrenheit during the course of the measurement.) For reference, Hardness has been found to relate strongly to the complex modulus of the material, which is a combination of the viscous and elastic moduli of the material.

6.7 Trans-topsheet Capacity

Figure 8:
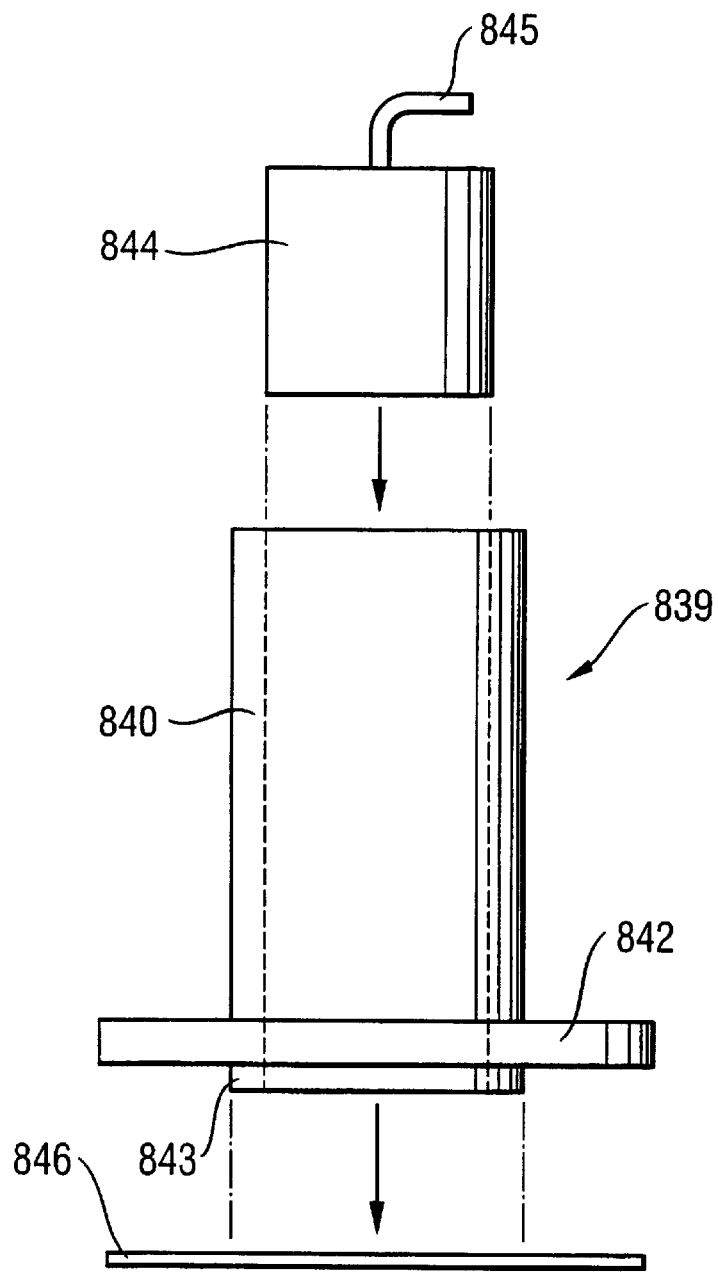
FIG. 8 is a schematic front view of an apparatus which may be used to measure trans-topsheet capacity characteristics of structures.

Trans-topsheet capacity is measured by the following test. The apparatus 839 used for this measurement is illustrated in FIG. 8. Faecal analogue A is used to measure Trans-topsheet capacity.

A hollow stainless steel cylinder 840 mounted on a plate 842 is provided. The stainless steel cylinder 840 has a height of 7.5 centimetres (2.95 inches), an inside diameter of 5.08 centimetres (2.00 inches) and an outside diameter of 6.3 centimetres (2.48 inches). The bottom of the cylinder 840 extends below the plate a distance of 3.5 millimetres, and has a lip with an annular thickness of 3.5 millimetres. The lip 843 prevents the faecal material analogue, discussed below, from leaking outside the designated test area of the sample.

Also provided is a weight 844 of 100.6 grams. The weight 844 is also cylindrically shaped and has a diameter of 5.08 centimetres (2.0 inches), so that the weight 844 fits tightly within the cylinder 840 but can freely slide throughout the hole in the cylinder 840. This arrangement provides a pressure of 49.57 kilograms per square meter (0.071 pounds per square inch) and a test area of 3.142 square inches. If desired, the weight 844 may have a handle 845 to allow it to be easily inserted into and removed from the cylinder 840.

A sample 846 to be tested is provided. The sample 846 is preferably cut from the second region 82 of an existing diaper 20, but prophetically may be supplied in raw material form as a laminate of the various components of the diaper 20. The sample 846 is cut to a 10.16 by 10.16 centimetres (4 by 4 inch) square size. The sample 846 is taken from any area of the diaper 20 having the liquid storage structure 28 inside the square which defines the sample 846.

If the sample 846 is cut from a diaper 20, the sample should include all layers and components of the diaper 20 from the topsheet 24 through and including the backsheet 26. Care must be taken when removing the sample 846 from the diaper 20 not to destroy the sample 846 or cause unintended gross deformation of the topsheet 24. The topsheet 24, or its equivalent in the diaper 20, is removed from the balance of the sample 846. The sample 846 (without the first topsheet 24) is weighed to the nearest 0.01 grams. The topsheet 24 is then carefully returned to its original position in the sample 846, without being joined thereto. If difficulty is encountered in removing the sample 846 from the diaper 20, or in removing the topsheet 24 from the sample 846, the sample 846 and the surrounding portion of the diaper 20 may be frozen prior to or after cutting. Freezing may be accomplished using PH100-15 circuit refrigerant made by Philips ECG, Inc. of Waltham, Mass.

The cylinder 840 is centred on the sample 846. A syringe having an opening of 5 to 6 millimetres dispenses 10 cubic centimetres of test fluid through the hole in the cylinder 840 onto the top of the sample 846. The test fluid is fecal analogue A formulated as described above having a zero shear viscosity between 10000 and 15000 CentiPoise. The 100.6 gram weight 844 is inserted through the hole in the cylinder 840 and gently placed on the test fluid for a period of 2 minutes.

After 2 minutes the weight 844 and cylinder 840 are removed from the sample 846. The topsheet 24 is removed from the sample 846 by dragging the topsheet 24 parallel to the sample 846 and discarded. The remainder of the sample 846 is then reweighed. The trans-topsheet capacity is the increase in weight of all layers of the sample 846 underlying the topsheet 24 divided by the sample 846 test area of 3.142 square inches.

6.8 Acceptance Under Pressure

Figure 5:
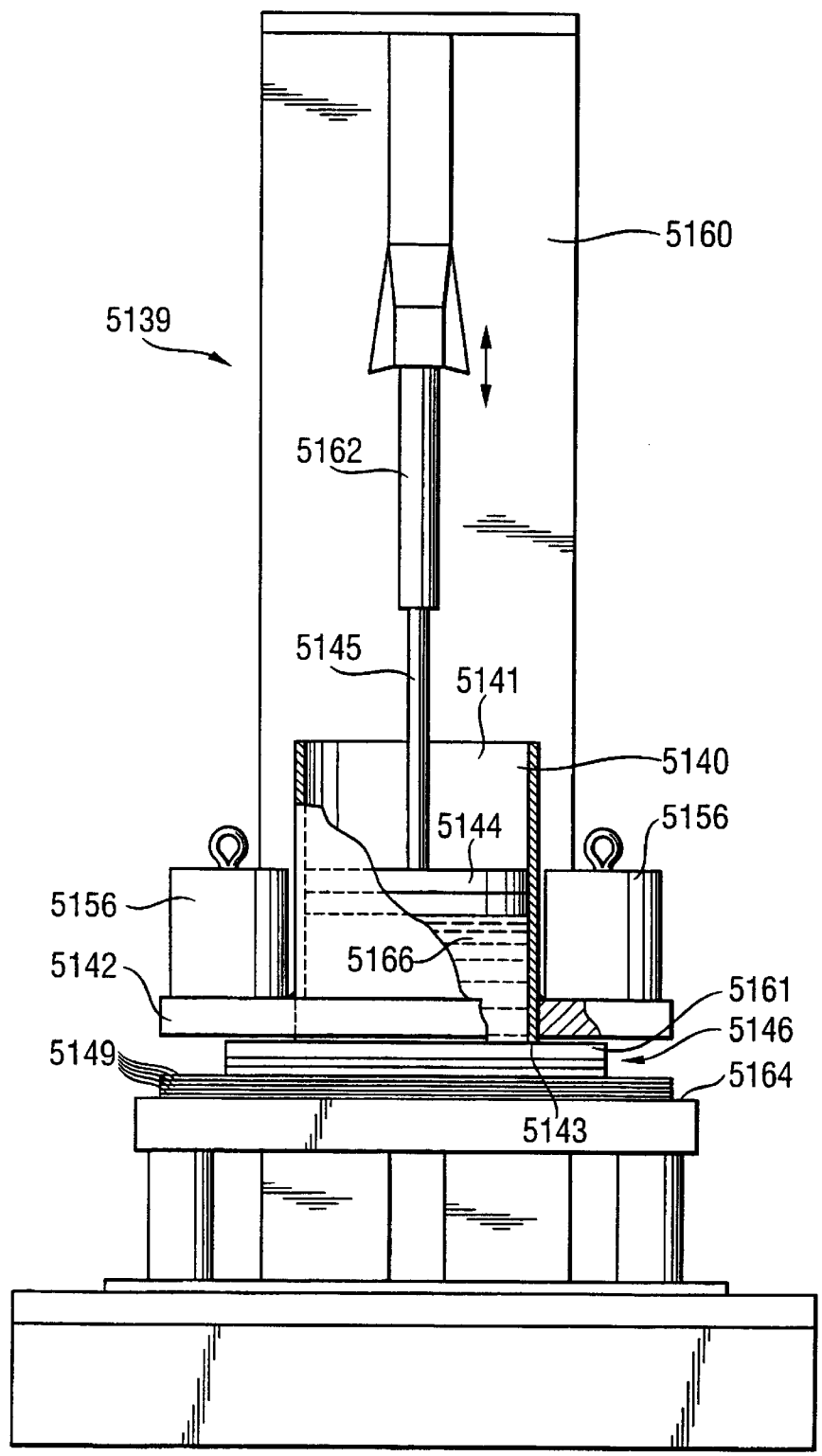
FIG. 5 is a schematic front view of an apparatus which may be used to measure Acceptance Under Pressure and Storage Under Pressure characteristics of structures.
Figure 6:
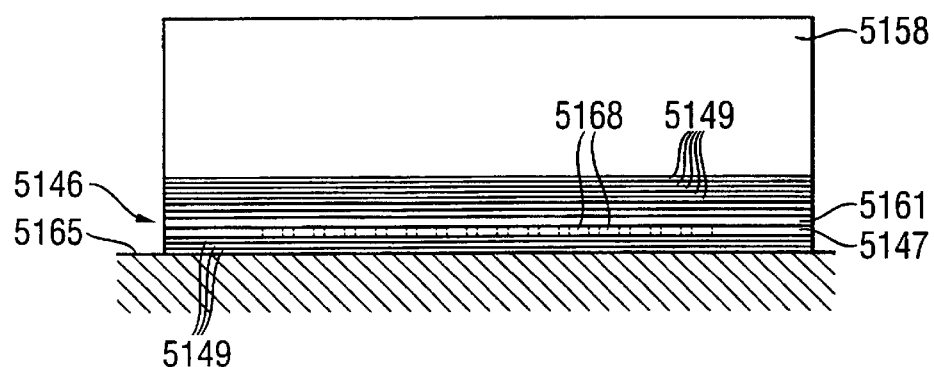
FIG. 6 is a schematic side view of an apparatus which may be used to measure retention and Immobilization Under Compressed Inversion characteristics of structures.

Acceptance Under Pressure is measured by the following test which uses the apparatus 5139 illustrated in FIG. 5. A hollow Plexiglas cylinder 5140 is provided mounted on a stainless steel plate 5142 about 9.5 mm thick. The plate 5142 is a square, about 10.16 cm×10.16 cm (about 4 in.×4 in.). The cylinder 5140 and plate combination has a height of 7.6 centimetres (about 3.0 inches), an inside diameter of 5.08 centimetres (about 2.00 inches) and an outside diameter of 6.3 centimetres (about 2.48 inches). The bottom of the cylinder 5140 extends below the plate 5142 a distance of about 3.5 millimetres. The lip 5143 prevents the test fluid 5166 from leaking outside the designated test area. Two 500 gram weights 5156 are also provided, each having a diameter of 5.08 cm (about 2.0 inches).

A cylindrically shaped 24.6 gram Plexiglas weight 5144 is provided. The weight 5144 has a diameter of 5.08 centimetres (about 2.0 inches), so that the weight 5144 fits with close tolerance within the cylinder 5140 but can freely slide throughout the hole 5141 in the cylinder 5140. This arrangement provides a pressure of about 119 Pascals (Pa) (about 0.017 pounds per square inch) and a test area of about 20.27 square cm (about 3.142 square inches). If desired, the weight 5144 may have a handle 5145 to allow it to be easily inserted into and removed from the cylinder 5140. In such cases, the combined mass of the handle 5145 and the cylindrical weight 5144 should equal 24.6 grams.

Figure 7:
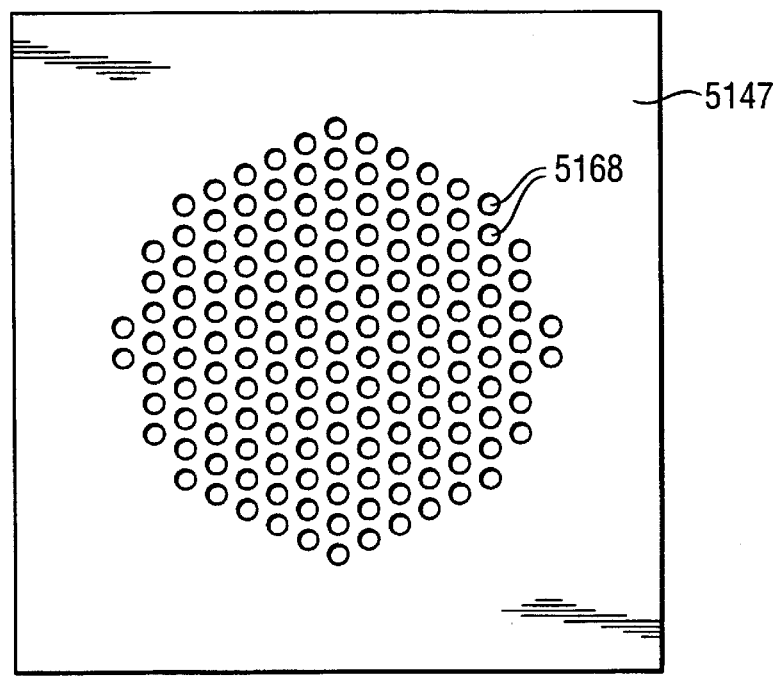
FIG. 7 is a plan view of a piece of a standard storage element.

A sample 5146 of the structure to be tested for Acceptance Under Pressure properties is provided. The sample 5146 may be cut from an existing diaper or may be constructed from material which has not been formed into a diaper. The sample 5146 includes the entire structure intended for use in an article or the entire structure of the article to be evaluated, including the top layer 5161. (In order to measure the Acceptance Under Pressure performance of discrete acceptance elements, as described in the Acceptance Element section above, the Acceptance Under Pressure test is performed using the standard storage element 5147 in place of any underlying structure or layers. The standard storage element 5147 used herein includes a 10.16 cm (4 inch) square 1.6 mm thick aluminium plate having a pattern of 153 regularly spaced 4.3 mm diameter holes 5168, as shown in FIG. 7. The holes are arranged such that there are about 26 holes per square inch.) The sample 5146 should be cut into a square measuring 10.16 centimetres by 10.16 centimetres (about 4 inches by 4 inches).

Five layers of a high basis weight blotter 5149 measuring 10.16 cm×10.16 cm (4 inches×4 inches) are provided. The top layer 5161 of the sample 5146 is removed and the remaining components, or layers, of the sample 5146 (if there are multiple components or layers) and the five sheets of blotter material 5149 are weighed to the nearest 0.01 grams. Thus, if the sample 5146 is being taken from a diaper, the layers of the diaper such as topsheets, secondary topsheets, acquisition layers, liquid storage structures etc., should be separated prior to weighing. (In some cases, a single layer may comprise two or more permanently bonded components.) In so doing, care must be taken not to destroy the sample 5146 or cause unintended gross deformation of any parts of the sample 5146. The layers of the sample 5146 may be frozen to aid their separation from adjacent layers of the sample 5146. Freezing may be accomplished using PH100-15 circuit refrigerant made by Philips ECG, Inc. of Waltham, Mass.

The sample 5146 should be reassembled as originally configured on top of 5 stacked layers of blotter material 5149 with the side of the sample 5146 intended to face the wearer oriented facing up and away from the blotter material 5149. The blotter material 5149 is preferably filtration grade paper, available from Ahlstrom Filtration, Inc. of Mt. Holly Springs, Pa. as #632-025, having a basis weight of about 90 grams per square meter.

The combined assembly of the sample 5146 and the blotter material 5149 is centred on the work surface 5164 of a Stevens-Farnell QTS-25 Model 7113-5 kg Texture Analyser 5160 (available from Leonard Farnell Co. of Hatfield, England), under the probe 5162. A suitable probe 5162 is a 100 cm flat-ended cylindrical aluminium extension rod "QTSM3100" available from the Leonard Farnell Co. of Hatfield England. The cylinder 5140 is centred on the sample 5146. The two 625 gram weights 5156 are placed on opposite corners (diagonally) of the plate 5142 to stabilise it. A syringe having an opening of about 4 to 6 millimetres is used to dispense approximately 10 cubic centimetres of viscous fluid bodily waste analogue 5166 (Analogue C as described above) through the hole 5141 in the cylinder 5140 onto the top of the sample 5146.

Once the proper amount of viscous fluid bodily waste analogue 5166, Analogue C, has been measured into the cylinder 5140, the 24.6 gram weight 5144 is inserted slowly and gently into the hole 5140 in the cylinder 5140 until it rests on the surface of the analogue. The Texture Analyser 5160 is activated so the probe 5162 depresses the cylindrical weight 5144 at a rate of 10 millimetres per minute until a resisting force of about 1.42N (144.6 grams of force) is reached. The Texture Analyser 5160 is set to stop the downward stroke once the resistance force of 1.42N (144.6 grams of force) is reached. The recorder is set to trigger at a resistive force of 0.049N (5 grams of force) thereby defining starting point $s_0$. The maximum resisting force of 1.42N (144.6 grams of force) corresponds to an applied pressure of 700 Pascals (0.1 pounds per square inch). Once a resistive force of 1.42N (144.6 grams of force) is reached, the probe 5162 is retracted to its starting position.

The weight 5144 is removed from the cylinder 5140, and then the cylinder 5140 is removed from the surface of the sample 5146, taking care not to drip any Analogue C remaining in the cylinder 5140 onto the sample. The top layer 5161 of the sample 5146 is then removed from the underlying layer(s) of the sample 5146 by dragging the top layer 5161 parallel to the surface of the underlying layers, if possible. For certain structures where the top layer 5161 is difficult to remove by dragging parallel to the underlying layers, the top layer 5161 may be peeled or lifted away from the underlying layers of sample 5146. If the sample 5146 comprises only a single layer, the standard acceptance element, described below, is utilised as the top layer 5161 of the sample 5146. The underlying layers of the sample 5146 and the blotter material 5149 are then weighed.

The acceptance under load $A_L$ of the sample 5146 equals the increase in combined weight of the underlying layer(s) of the sample 5146 and the blotter material 5149 caused by the test Analogue C penetrating through the top surface layer of the sample 5146 per work W performed (in millijoules) on a unit area basis. The work W is calculated by integrating the force F(s) resisting the probe on its downward stroke from the starting point at $s_0$ over the total distance travelled until the maximum force of 1.42N (144.6 grams of force) is registered at $s_{max}$. The unit work is calculated using the following equation:

$$W = \int_{s_0}^{s_{max}} F(s)ds$$

6.9 Storage Under Pressure

Storage Under Pressure is measured using the same apparatus 5139 described above and illustrated in FIG. 5. The hollow cylinder 5140, weight 5144, and 625 g weights 5156 described in the Acceptance Under Pressure test above are provided. A sample 5146 of the structure to be tested for Storage Under Pressure properties is also provided. Again, the sample 5146 may be cut from an existing diaper 20 or may be constructed from material which has not been formed into a diaper. The sample 5146 should include the entire structure intended for use in an article or the entire structure of the article to be evaluated. (In order to measure the Storage Under Pressure performance of discrete storage elements, as described in the Storage Element section above, the Storage Under Pressure test is performed using the standard acceptance element in place of any overlying structure or layers. The standard acceptance element 150 is a stainless-steel wire cloth Type 304 (Standard Grade) 16×16 mesh, available as #9226T45 from McMaster Carr Supply Company of Chicago, Ill.) The sample 5146 should be cut into a square measuring 10.16 centimetres by 10.16 centimetres (about 4 inches by 4 inches).

Five layers of a high basis weight blotter 5149 (identical to that described in the Acceptance Under Pressure test above) measuring 4 inches×4 inches are provided. The top layer 5161 of the sample 5146 is removed and the remaining components, or layers, of the sample 5146 (if there are multiple components or layers) and the five sheets of blotter material 5149 are weighed to the nearest 0.01 grams. Thus, if the sample 5146 is being taken from a diaper, the top layer 5161 of the diaper, such as the topsheet, should be separated from the sample 5146 prior to weighing. In so doing, care should be taken not to destroy the sample 5146 or cause unintended gross deformation of the elements of sample 5146. The layers of the sample 5146 may be frozen, as described above, to aid their separation from adjacent layers of the sample 5146.

The sample 5146 should be reassembled as originally configured on top of five stacked sheets of blotter material 5149 with the side intended to face the wearer oriented facing up and away from the blotter material 5149. The combined assembly of the sample 5146 and the blotter material 5149 is centred on the work surface 5164 of the Texture Analyser 5160 (described above), under the probe 5162. The cylinder 5140 is centred on the sample 5146. The two 625 gram weights 5156 are placed on diagonally opposite corners of the plate 5142 to stabilise it. A syringe having an opening of about 4 to 6 millimetres is used to dispense 10 cubic centimetres Analogue C (as described above) through the hole in the cylinder 5140 onto the top of the sample 5146. The 24.6 gram weight 5144 is inserted into the hole 5141 in the cylinder 5140 and the Texture Analyser 5160 is activated with the probe 5162 depressing the cylindrical weight 5144 at a rate of 10 millimetres per minute until a resisting force of 1.42N (144.6 grams of force) is reached. (The maximum resisting force of 1.42N (144.6 grams of force) corresponds to an applied pressure of 700 Pascals or 0.1 pounds per square inch). Once the resisting force of 1.42N (144.6 grams of force) is reached, the probe 5162 is retracted to its starting position.

The weight 5144 is removed from the cylinder 5140, and then the cylinder 5140 and weights 5156, are removed from the surface of the sample 5146, taking care not to drip any Analogue C remaining in the cylinder 5140 onto the sample. The sample 5146 is then removed from the work surface 5164 of the Texture Analyser 5160 by dragging the sample 5146 parallel to the work surface 5164, if possible. For certain structures where the top layer 5161 is difficult to remove by dragging parallel to the underlying layers, the top layer 5161 may be peeled or lifted away from the underlying layers of sample 5146. The sample 5146 and the blotter 5149 are then weighed. The amount of test Analogue C 5166 stored equals the increase in combined weight of the underlying layers of the sample 5146 and the blotter 5149 caused by the test Analogue C penetrating into the sample 5146 on a unit area basis.

6.10 Immobilisation and Retention Under Compressed Inversion

To measure Immobilisation Under Compressed Inversion and Retention Under Compressed Inversion, a cylinder 5140 is mounted on plate 5142 as shown in FIG. 5. The cylinder 5140 has a height of 7.5 centimetres (about 2.95 inches), an inside diameter of 5.08 centimetres (about 2.00 inches) and an outside diameter of 6.3 centimetres (about 2.48 inches). The hollow cylinder 5140 and plate 5142 are identical to those used in the Acceptance Under Pressure and Storage Under Pressure tests described above, with the exception that the plate does not have the "lip" 5143 on the bottom, and that both the cylinder 5140 and the plate 5142 are made of stainless steel. The stainless steel cylinder 5140 and plate 5142 have a combined weight of about 1170 grams.

The sample 5146 of the structure to be tested is provided and the top layer 5161, if included in the sample 5146, is removed. The remaining underlying layers of the sample 5146 and the five layers of blotter material 5149 are assembled and weighed. The top layer 5161 is then placed on top of this assembly. The sample 5146 may also be made from materials that have not been made into a structure. The combined assembly of the sample 5146 to be tested and blotter 5149 is placed on a benchtop 5165. (In order to measure the Immobilisation Under Compressed Inversion and Retention Under Compressed Inversion performance of discrete immobilisation and retention elements, as described in the Immobilisation Element section above, the Immobilisation Under Compressed Inversion test is performed using the standard acceptance element in place of any top layer 5161. All underlying layers are included in this evaluation.) A syringe having an opening of about 4 to 6 millimetres is used to dispense 10 cubic centimetres of test analogue through the hole in the cylinder 5140 onto the top of the sample 5146.

The test analogue (Analogue B) is allowed to penetrate the sample 5146 under gravitational force for 3 minutes. The cylinder 5140 is then removed from the surface of the sample 5146 and the entire sample 5146 is weighed. The top layer 5161 of the sample 5146 is then removed from the underlying layers of the sample 5146 by lifting the top layer 5161 vertically from the surface of the underlying layers and allowing any excess Analogue B to drain back into the lower layers. The assembly of the remainder of sample 5146 and the blotter material 5149 is then weighed. This provides a measure of the net quantity of Analogue B $Q_B$ imbibed by the structure during the loading step of this test. The sample 5146 is then reassembled, including the top surface layer 5161. Three layers of the 4 inch square blotter material 5149 are provided and weighed. A standard storage element 5147 is provided and placed on top of the three layers of blotter material 5149. The reassembled sample 5146 is inverted onto the assembly of the standard storage element 5147 and the three layers of blotter material 5149. (The standard storage element 5147 includes a 4 inch square 1.6 millimetre thick aluminium plate having a pattern of 5153 regularly spaced 4.3 millimetre diameter holes 5168, as shown in FIG. 7. The holes are arranged such that there are approximately 26 holes per square inch.)

A 16 pound, 16 square inch weight 5158 (corresponding to a 7000 Pascal pressure, or 1.0 psi) is then gently placed on the surface of the sample 5146 which is facing away from the standard storage element 5147. The weight 5158 is removed after three minutes, and the sample 5146 is reoriented so that the side insulted by the test Analogue B is facing up. The top layer 5161 is removed and the weight of the remaining layers of sample 5146 and the five layers of blotter material are measured and recorded. The sample's Retention Under Compressed Inversion $R_{CI}$ is calculated as the actual net amount of test Analogue B present in the underlying layers of the structure after the inversion cycle.

Immobilisation Under Compressed Inversion $I_{CI}$ is calculated as the percentage of the test Analogue B that penetrated the structure (i.e., passed through the surface layer into the underlying layers of the sample) during the loading step which remains in the underlying layers of the structure after the inversion step. The equation for determining Immobilisation Under Compressed Inversion is as follows:

$$I_{CI} = \frac{R_{CI}}{Q_B}$$

6.11 Surface Tension Measurement

All measurements were done on a commercially available digital tensiometer, Type K 10 T of Krüss GmbH, Germany, applying the well known ring method. Thereby, the force to pull a circular ring of platinum immersed into the test liquid upwards is monitored, and while considering gravity and buoyancy the surface tension is determined, expressed in N/cm.

All glassware and the platinum ring is cleaned with isopropanol and deionized water and then dried in a drying oven at 50° C. Shortly before performing the measurement, the glassware is further cleaned and dried by using a Bunsen burner flame, and then cooled down to 37° C. in a desiccator.

All measurements are done at 37° C., by heating the test solution and the sample holder to 37° C.

The glass beaker of the equipment is filled with 25 ml (+/−5 ml) test solution (preferably directly from the main reservoir without using an transfer tool like a burette) and placed in the sample holder. Then the platinum ring is heated until red heat in the flame of a Bunsen burner and immediately put into the ring holding device.

The equipment is then initiated to automatically perform the measurement, i.e. immersing and pulling of the ring at a constant speed while measuring the forces. The result can be directly read from the display of the equipment.

Unless otherwise noted, each measurement is replicated 3 times, and the results are averaged.

6.12 Surface Tension Reduction Measurement

The surface tension reduction test of the present invention is intended to measure the impact of one of the components of the absorbent article of the present invention on the surface tension of an acquired liquid.

All glassware and the platinum ring is cleaned with isopropanol and deionized water and then dried in a drying oven at 50° C. Shortly before performing the measurement, the glassware is further cleaned and dried by using a Bunsen burner flame, and then cooled down to 37° C. in a desiccator.

At the beginning of the test, the surface tension of 40 ml of deionized water is measured via the above surface tension test. Then, 3 samples of the component to be tested are immersed into the 40 ml of deionized water. The sample of the component shall weigh about 0.05 gram. The configuration of the sample should resemble as closely as possible the configuration of the component in the absorbent article, in particular in terms of surface area accessible to the acquired liquid. In case, the sample of the components weighs less than 0.05 gram the amount of test liquid has to be adjusted accordingly. After 5 minutes, the sample is completely removed from the test liquid. The surface tension of the remaining liquid is measured three times.

The surface tension reduction of the tested component of the absorbent article is the difference between the initial surface tension and the final surface tension of the deionized water.

6.13 Method to Determine Effective Aperture Size and Open Area of a Structured Carrier The effective aperture size and effective open area are determined by the following procedure using the image analysis described below. The procedure has three principal steps: image acquisition, i.e., obtaining representative images of areas on the surface of the structured carrier 24; image measurement, i.e., measuring the percentage open area of an image and of individual apertures and their perimeters; and data analysis, i.e., exporting the percentage open area, individual aperture area, and perimeter measurements to a spreadsheet where frequency distributions, sum of area distributions, and hydraulic radius computations are made.

An image analysis system having a frame grabber board, microscope, camera and image analysis software is utilised. A model DT2855 frame grabber board available from Data Translation of Marlboro, Mass. is provided. A VH5900 monitor microscope, a video camera, having a VH50 lens with a contact type illumination head available from the Keyence Company of Fair Lawn, N.J., USA are also provided and used to acquire an image to be saved to computer file. The Keyence microscope acquires the image and the frame grabber board converts the analogue signal of this image into computer readable digital format. The image is saved to computer file and measured using suitable software such as the Optimas Image Analysis software, version 3.1, available from the BioScan Company of Edmaons, Wash. In order to use the Optimas Image Analysis software, the computer should have Windows software, version 3.0 or later, available from the Microsoft Corporation of Redmond, Wash. And also have a CPU at least equivalent to the Intel 80386. Any suitable desk top PC may be used, with a 486 DX33 type PC having been found to be particularly suitable. Images being saved to and recalled from file were displayed on a Sony Trinitron monitor model PVM-1343MO with a final display magnification of about 50x.

The image acquisition step, noted above requires 10 different regions from a representative structured carrier 24 sample of a particular type of diaper 20 or from sample material to be tested. Each region is rectangular, measuring about 5.8 millimetres by 4.2 millimetres. The sample is placed on a black mat board to increase the contrast between the apertures and the portion of the sample which defines the apertures. The mean grey level and standard deviation of the black mat board were 16 and 4, respectively.

Images are acquired with room lights off using the Keyence monitor microscope mounted on a copystand directly above the sample. The Keyence light source illuminating the sample is adjusted and monitored with the Optimas software to measure the mean grey level and standard deviation of a 0.3 density wedge on a Kodak Grey Scale available from Eastman Kodak Company of Rochester, N.Y. The control of Keyence light source is adjusted so that the mean grey level of the illuminated wedge is 111+1 and the standard deviation is 10+1. All images were acquired during a single time period, and the Keyence light source is monitored by measuring the mean grey level and standard deviation of the wedge throughout the image acquisition process.

In measuring an individual aperture, only the effective aperture size is of interest. Measuring the effective aperture size quantifies the aperture size intended to contribute to the porosity of the structured carrier 24, and account for contributions of fibres and fibre bundles which traverse an area intended to be an aperture. An effective aperture is any hole through the structured carrier 24 having a grey level less than or equal to 18 using image acquisition parameters as described herein. Thus, an intended aperture may be divided into plural effective apertures by traverse fibres.

The image analysis software is calibrated in millimetres by a ruler image acquired from the sample images. A 3 by 3 pixel averaging filter found in the Optimas 3.1 Image menu is applied to each saved image to reduce noise. The apertures are detected in the grey level range of 0 through 18. An aperture which is not fully contained within the 5.8 by 4.2 viewing area is not considered in the individual area and perimeter measurements. Therefore, area and perimeter averages and distributions are not affected by apertures which are not wholly contained within the field of view.

However, individual apertures which could not be fully viewed in the image are included in the percentage open area calculation. This difference occurs because the percent open area is simply the image of pixel ratios from 0 through 18 to the total number of pixels in the image. Areas having a grey level 19 or greater were not counted in the open area calculation.

The percentage open area for the average of 10 images for each structured carrier 24 is measured using the Optimas Image Analysis software. The percentage open area is defined as the ratio of the number of pixels having a grey level from 0 through 18 to the total number of pixels for the image. The percentage open area is measured for each image representing one particular region from a structured carrier sample. The percentage open area from each of the 10 individual images is then averaged to yield a percentage open area for the entire sample.

The data analysis is conducted by an Excel spreadsheet, also available from the Microsoft Corporation of Redmond, Washington. The Excel spreadsheet organised the percentage open area, aperture area, and aperture perimeter measurements obtained from the Optimas software. Sample averages and standard deviations, size and frequency distributions of individual aperture areas and hydraulic radius computations (area divided by perimeter) for individual apertures are obtained using the spreadsheet.

Distributions of individual aperture area are also computed using the Excel spreadsheet. The apertures are sorted into bins of certain size ranges. The number of aperture areas falling into certain size ranges of interest is determined as well as the sum of the areas within each range. The ranges are set in increments of 0.05 square millimetres. These areas are expressed as a percentage of the total open area of the sample. The frequency and sum of the area distributions are obtained by combining individual aperture measurements from all 10 images for each sample.

What is claimed is:

1. A disposable absorbent article having a transverse centerline, a first region, and a second region and a front region and a ear region, said front region being positioned forward of said transverse centerline, said front region coming into contact with the front waist of the wearer during use, said back region being positioned backward of said transverse centerline, said back region coming into contact with the back waist of the wearer during use, said disposable absorbent article comprising a liquid pervious, fibrous, structured carrier, a liquid impervious backsheet at least partially peripherally joined to said structured carrier, a liquid storage structure positioned intermediate said structured carrier and said backsheet, a liquid handling structure positioned intermediate said structured carrier and said liquid storage structure, a portion of said liquid handling structure being positioned in said first region, a portion of said liquid handling structure being positioned in said second region, said structured carrier having a liquid retention of less than 150 mg for a test liquid having a surface tension of 33 mN/m, and said liquid handling structure having a basis weight to uncompressed calliper ratio of less than 100 grams per square meter per millimeter.

2. A disposable absorbent article according to claim 1 wherein said structured carrier has a liquid retention of less than less than 50 mg for a test liquid having a surface tension of 62 mN/m.

3. A disposable absorbent article according to claim 1 wherein said disposable absorbent article has a front region total product acquisition performance of more than 3.75 ml/s in the first gush and of more than 0.5 ml/s in the fourth gush.

4. A disposable absorbent article according to claim 1 wherein said disposable absorbent article has a front region Skin Hydration rewet value of less than 120 milligrams.

5. A disposable absorbent article according to claim 1 wherein said structured carrier has a contact angle with distilled water of more than 90°.

6. A disposable absorbent article according to claim 1 wherein said liquid handling structure has a compression resistance of at least 70% under an applied pressure of 1 Newton per square centimeter.

7. A disposable absorbent article according to claim 1, wherein at least a part of a surface of said structured carrier which faces the wearer during use comprises a surface finish selected from the group of fluoropolymers, chiorofluoropolymers, and silicone coatings.

8. A disposable absorbent article according to claim 1 wherein said structured carrier comprises a plurality of apertures having a size of at least 0.2 mm$^2$.

9. A disposable absorbent article according to claim 1 wherein said structured carrier has a open area of more than 12%.

10. A disposable absorbent article according to claim 5 wherein said structured carrier comprises a layer of nonwoven material.

11. A disposable absorbent article according to claim 1 wherein said structured carrier comprises a skin care composition which is at least partially transferable to the skin of a wearer during use.

* * * * *

UNITED STATES PATENT AND TRADEMARK OFFICE
CERTIFICATE OF CORRECTION

PATENT NO. : 6,706,946 B1
DATED : March 16, 2004
INVENTOR(S) : John Peter Lankof and Mattias Schmidt It is certified that error appears in the above-identified patent and that said Letters Patent is hereby corrected as shown below:

Column 7,
Line 4, delete "Modem" and insert therefor -- Modern --.

Column 20,
Line 30, delete "the'skin" and insert therefor -- the skin --.

Column 23,
Line 16, delete "microporou s" and insert therefor -- microporous --.

Column 31,
Line 11, delete "Famell" and insert therefor -- Farnell --.

Column 37,
Line 10, delete "ear" and insert therefor -- rear --.

Column 38,
Line 18, delete "chiorofluoropolymers" and insert therefor -- chloroflurorpolymers --.

Signed and Sealed this

Twentieth Day of July, 2004

JON W. DUDAS
*Acting Director of the United States Patent and Trademark Office*